US009824444B2

(12) United States Patent
Kubo

(10) Patent No.: US 9,824,444 B2
(45) Date of Patent: Nov. 21, 2017

(54) IMAGE PROCESSING APPARATUS

(71) Applicant: OLYMPUS CORPORATION, Tokyo (JP)

(72) Inventor: Kei Kubo, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/293,531

(22) Filed: Oct. 14, 2016

(65) Prior Publication Data
US 2017/0032521 A1 Feb. 2, 2017

Related U.S. Application Data

(63) Continuation of application No. PCT/JP2015/075085, filed on Sep. 3, 2015.

(30) Foreign Application Priority Data

Mar. 26, 2015 (JP) .................................. 2015-064542

(51) Int. Cl.
G06T 7/00 (2017.01)
A61B 1/00 (2006.01)
(Continued)

(52) U.S. Cl.
CPC ........ *G06T 7/0012* (2013.01); *A61B 1/00009* (2013.01); *A61B 1/043* (2013.01);
(Continued)

(58) Field of Classification Search
CPC ..... G06T 7/0016; G06T 7/0012; G02B 23/24; A61N 5/06; A61N 5/04; A61B 1/00
See application file for complete search history.

(56) References Cited

U.S. PATENT DOCUMENTS 5,475,420 A * 12/1995 Buchin ................ A61B 1/0005
  348/65
8,073,212 B2 * 12/2011 Gerlach ............... A61B 5/0088
  382/128
(Continued)

FOREIGN PATENT DOCUMENTS

EP   1929930 A1   6/2008
EP   2422688 A1   2/2012
(Continued)

OTHER PUBLICATIONS

International Search Report dated Nov. 24, 2015 issued in PCT/JP2015/075085.

*Primary Examiner* — Chan Park
*Assistant Examiner* — Mia M Thomas
(74) *Attorney, Agent, or Firm* — Scully, Scott, Murphy & Presser, P.C.

(57) ABSTRACT

An image processing apparatus includes an input section, a specification section, an extraction section, and a calculation section. The input section receives fluorescence image information obtained by picking up an image of fluorescence based on application of excitation light to a subject provided with a fluorescent substance with a specific effect on a living tissue and therapeutic light position image information including an application position of therapeutic light. The specification section specifies an application region of the therapeutic light. The extraction section extracts a luminance value corresponding to the application region of the therapeutic light and a luminance value corresponding to a region other than the application region of the therapeutic light. The calculation section calculates and outputs a ratio of the extracted luminance value corresponding to the application region to the luminance value corresponding to the region other than the application region.

20 Claims, 18 Drawing Sheets

(51) Int. Cl.
*A61N 5/06* (2006.01)
*G02B 23/24* (2006.01)
*A61B 1/04* (2006.01)
*A61B 1/06* (2006.01)
*A61B 5/00* (2006.01)

(52) U.S. Cl.
CPC .......... *A61B 1/0638* (2013.01); *A61B 5/0071* (2013.01); *A61N 5/06* (2013.01); *G02B 23/24* (2013.01); *G06T 7/0016* (2013.01); *G06T 2207/10016* (2013.01); *G06T 2207/10064* (2013.01); *G06T 2207/10068* (2013.01); *G06T 2207/10152* (2013.01); *G06T 2207/30096* (2013.01)

(56) References Cited

U.S. PATENT DOCUMENTS

| | | | | |
|---|---|---|---|---|
| 8,792,691 | B1* | 7/2014 | Rozenfeld | G06T 7/246 382/128 |
| 9,412,054 | B1* | 8/2016 | Krupnik | A61B 1/00009 |
| 2006/0106435 | A1* | 5/2006 | Fraval | A61B 5/0059 607/88 |
| 2006/0142657 | A1* | 6/2006 | Quaid | A61N 1/372 600/424 |
| 2007/0135874 | A1* | 6/2007 | Bala | A61B 1/00096 607/94 |
| 2008/0316427 | A1* | 12/2008 | Fisher | G06F 17/5009 351/233 |
| 2009/0028407 | A1* | 1/2009 | Seibel | A61B 1/0008 382/131 |
| 2009/0097725 | A1* | 4/2009 | Krupnik | A61B 1/00096 382/128 |
| 2009/0105579 | A1* | 4/2009 | Garibaldi | A61B 1/00158 600/409 |
| 2009/0156901 | A1 | 6/2009 | Gono | |
| 2009/0318760 | A1* | 12/2009 | Pascal | A61B 1/00009 600/117 |
| 2010/0329524 | A1* | 12/2010 | Swartling | A61N 5/0601 382/128 |
| 2011/0218597 | A1* | 9/2011 | Wang | A61N 5/06 607/89 |
| 2011/0242301 | A1* | 10/2011 | Morita | A61B 1/00009 348/65 |
| 2013/0197611 | A1* | 8/2013 | Swartling | A61B 5/0073 607/88 |
| 2013/0266202 | A1* | 10/2013 | Yamada | A61B 6/032 382/131 |
| 2016/0015471 | A1* | 1/2016 | Piron | G06T 7/70 600/424 |
| 2016/0101294 | A1* | 4/2016 | Sun | A61N 5/0616 607/88 |
| 2016/0270656 | A1* | 9/2016 | Samec | A61B 3/085 |

FOREIGN PATENT DOCUMENTS

| | | |
|---|---|---|
| JP | 2007-097649 A | 4/2007 |
| JP | 2011-045461 A | 3/2011 |
| JP | 2011-167229 A | 9/2011 |
| JP | 2011-167344 A | 9/2011 |
| JP | 2012-050602 A | 3/2012 |
| JP | 2012-125492 A | 7/2012 |
| JP | 2014-113232 A | 6/2014 |
| WO | WO 2007/039981 A1 | 4/2007 |

* cited by examiner

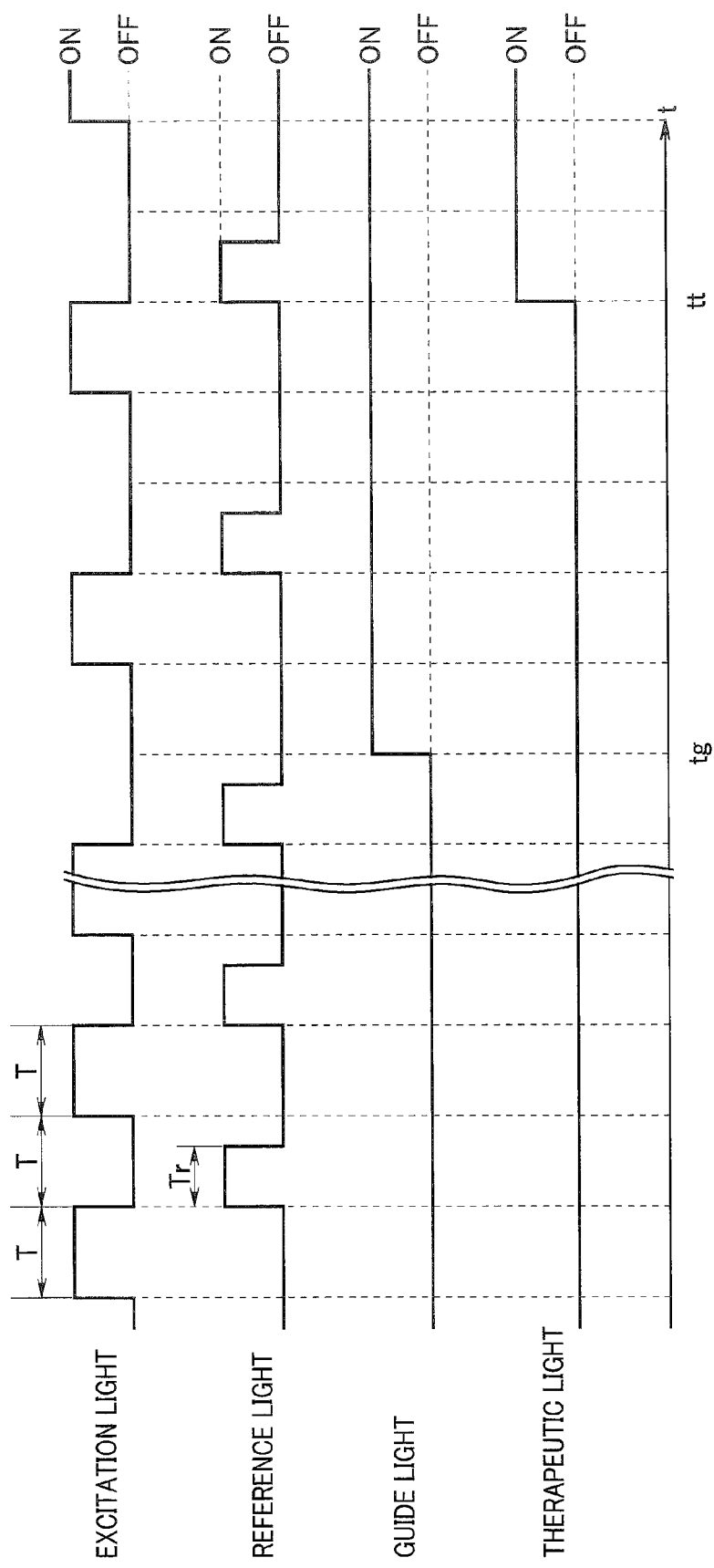

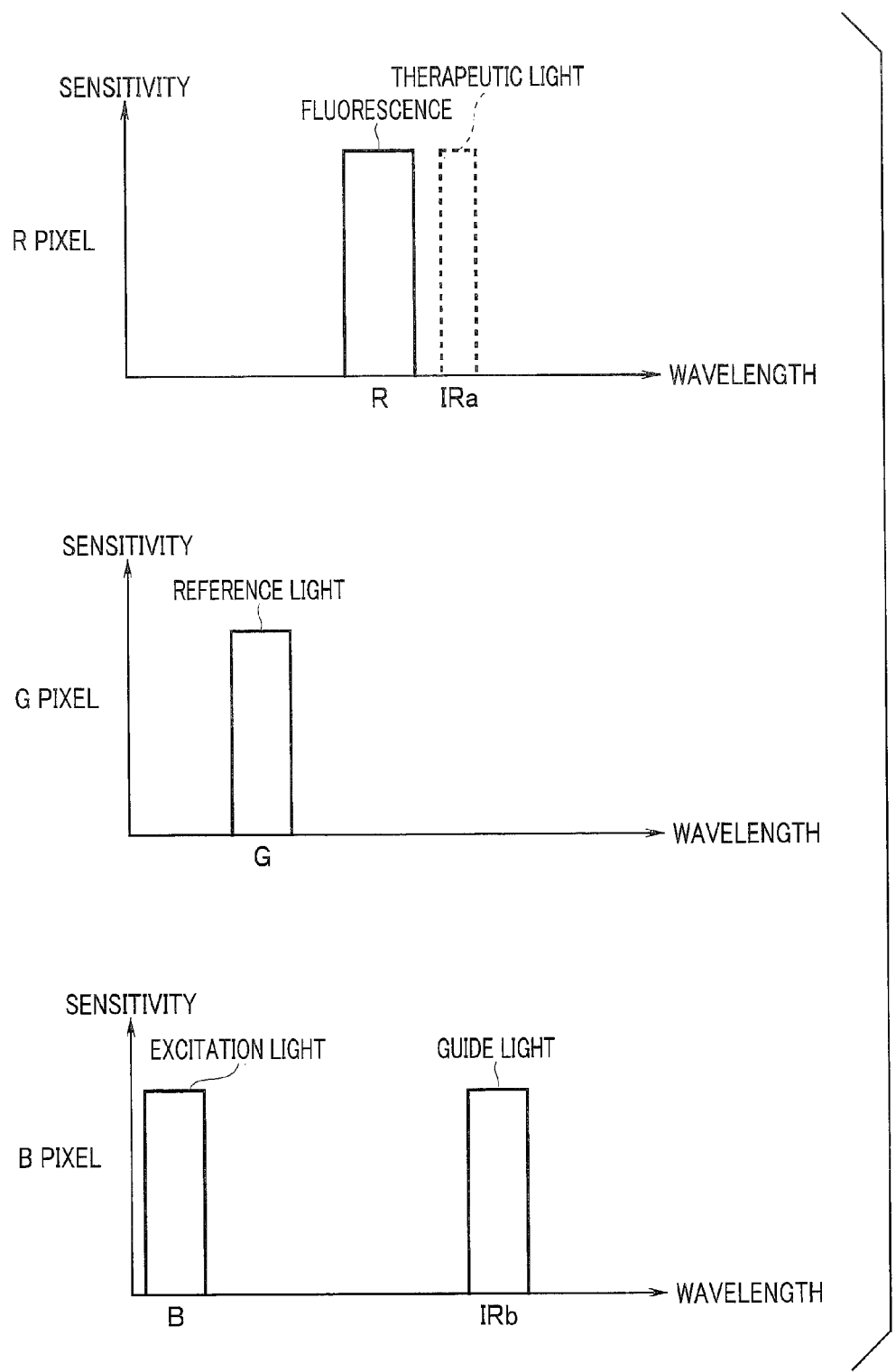

IMAGE PROCESSING APPARATUS

CROSS REFERENCE TO RELATED APPLICATION

This application is a continuation application of PCT/JP2015/075085 filed on Sep. 3, 2015 and claims benefit of Japanese Application No. 2015-064542 filed in Japan on Mar. 26, 2015, the entire contents of which are incorporated herein by this reference.

BACKGROUND OF THE INVENTION

1. Field of the Invention

The present invention relates to an image processing apparatus configured to apply image processing to a fluorescence image after application of therapeutic light.

2. Description of the Related Art

In recent years, an endoscope apparatus has been widely used in a medical field and the like. A method of performing photodynamic diagnosis (PDD) by using a photosensitive substance that is easily accumulated on a lesion site, such as a tumor site, in a living body and that generates fluorescence after application of excitation light is known. A method of performing photodynamic therapy (PDT) for a lesion site diagnosed by the PDD is known. A treatment method called PIT (photoimmuno therapy) is also known. In the treatment method, a wavelength of excitation light of an agent (fluorescent substance) and a wavelength of therapeutic light for performing an optical treatment are the same.

For example, Japanese Patent Application Laid-Open Publication No. 2014-113232 as a first conventional example discloses an optical treatment apparatus including: a light application section configured to excite a photosensitive substance to generate fluorescence and configured to apply first output light (excitation light) to be applied to an observation region and second output light (therapeutic light) to be applied to a treatment site; an image pickup section configured to pick up an image of the observation region; a photographic image generation section configured to generate photographic image data based on an image pickup signal from the image pickup section; a treated image generation section configured to generate treated image data indicating a position of application of the second output light; an image combination/display processing section configured to generate combined image data by superimposing the treated image data on the photographic image data; and a display section configured to display the combined image data as a combined image. A surgeon can easily figure out a treated site and an untreated site.

Japanese Patent Application Laid-Open Publication No. 2012-50602 as a second conventional example discloses an electronic endoscope system including: white light application means configured to apply white light into a subject; therapeutic light application means configured to act on a photosensitive substance accumulated on a site to be treated in the subject to apply therapeutic light for treating the site to be treated; an image pickup device configured to photoelectrically convert light entering from inside of the subject to pick up an image of the inside of the subject; light quantity adjustment means configured to adjust a light quantity of the therapeutic light to a low light quantity that does not generate halation; extraction means configured to extract data regarding a distribution of an application position and an application intensity of low light quantity therapeutic light adjusted to the low light quantity by the light quantity adjustment means from an image obtained by taking an image after applying the white light and the low light quantity therapeutic light into the subject; display means configured to display the image; and display control means configured to display the data extracted by the extraction means on the display means along with the image. An application efficiency of the therapeutic light is displayed, and an application position and a direction of the therapeutic light can be adjusted in advance to make the application efficiency of the therapeutic light excellent.

SUMMARY OF THE INVENTION

An aspect of the present invention provides an image processing apparatus including: an input section configured to receive fluorescence image information obtained by picking up an image of fluorescence based on application of excitation light to a subject provided with a fluorescent substance with a specific effect on a living tissue and therapeutic light position image information including an application position of therapeutic light for causing the fluorescent substance to make an effect on a living body; a specification section configured to specify an application region as a region of the application position of the therapeutic light in the fluorescence image information based on the therapeutic light position image information inputted to the input section; an extraction section configured to extract a luminance value corresponding to the application region of the therapeutic light specified by the specification section in the fluorescence image information inputted to the input section and a luminance value corresponding to a region other than the application region in the fluorescence image information; and a calculation section configured to calculate and output a ratio of the luminance value corresponding to the application region extracted by the extraction section to the luminance value corresponding to the region other than the application region.

BRIEF DESCRIPTION OF THE DRAWINGS

FIG. 5 is a diagram showing timings of generating the excitation light, the reference light, the guide light, and the therapeutic light in the first embodiment;

FIG. 15 is a diagram showing bands that R, G, and B pixels in an image pickup device including color filters are sensitive in the wavelength bands and the like of illuminating light;

DETAILED DESCRIPTION OF THE PREFERRED EMBODIMENTS

Hereinafter, embodiments of the present invention will be described with reference to the drawings.

First Embodiment

Figure 1:
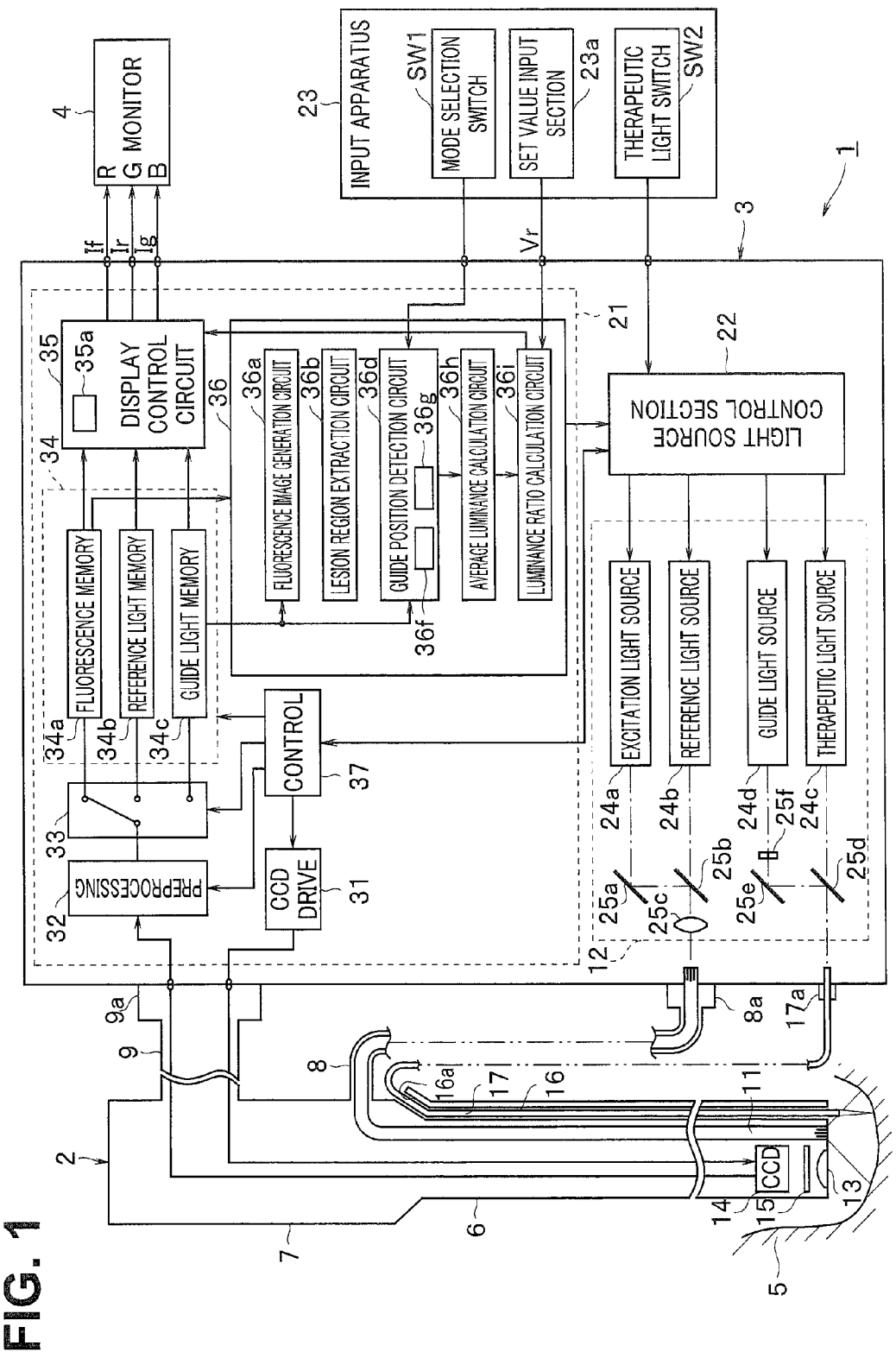
FIG. 1 is a diagram showing an overall configuration of an endoscope apparatus including an image processing apparatus of a first embodiment of the present invention.

As shown in FIG. 1, an endoscope apparatus 1 of a first embodiment including an image processing section (or image processing unit) 21 of the first embodiment of an image processing apparatus of the present invention includes: an endoscope 2 inserted into a body cavity; a control apparatus 3 to which the endoscope 2 is detachably connected, the control apparatus 3 configured to supply illuminating light and the like toward the endoscope 2 and apply signal processing to an image pickup section mounted on the endoscope 2; and a monitor 4 as a display apparatus configured to receive an image signal generated by the control apparatus 3 to display an image picked up by the image pickup section as an observed image.

The endoscope 2 includes: an elongated insertion portion 6 inserted into a subject 5; an operation portion 7 provided on a back end (proximal end) of the insertion portion 6; and a light guide cable 8 and a signal cable 9 extended from the operation portion 7. A light source connector 8a on an end portion of the light guide cable 8 and a signal connector 9a on an end portion of the signal cable 9 are detachably connected to the control apparatus 3.

A light guide 11 configured to transmit (or guide) illuminating light is inserted into the insertion portion 6, and a back end of the light guide 11 reaches the light source connector 8a. A light source section (or light source unit) 12 in the control apparatus 3 inputs (supplies) illuminating light to the back end of the light guide 11.

The inputted illuminating light is transmitted by the light guide 11, and from a distal end surface arranged on an illuminating window provided on a distal end portion of the insertion portion 6, the illuminating light is spread and applied toward an observation site, such as a diseased part, in the subject 5 facing the distal end surface. Note that the light guide 11 transmits inputted excitation light for fluorescence observation and reference light for acquiring morphological information of living tissue as the illuminating light (for acquiring a fluorescence image and a reference light image).

An objective lens 13 is arranged on an observation window provided adjacent to the illuminating window, and an optical image of fluorescence emitted from the site side provided with the excitation light is formed on an image pickup surface of a charge coupled device (abbreviated as CCD) 14 as an image pickup device. When the reference light is applied, an optical image of reflected light reflected by the applied site is formed on the image pickup surface of the CCD 14. Note that in the present embodiment, a monochrome CCD 14 not including a color filter is used as the image pickup device.

An excitation light cut filter 15 configured to cut the excitation light is arranged in an optical path between the objective lens 13 and the image pickup surface of the CCD 14. Therefore, when the excitation light and the reference light are applied to the observation site as described above, the light of the excitation light reflected by the observation site side is cut by the excitation light cut filter 15.

In the endoscope 2, a treatment instrument insertion port 16a is also provided near the back end of the insertion portion 6, and the treatment instrument insertion port 16a communicates with a treatment instrument channel 16 provided in a longitudinal direction of the insertion portion 6. In the present embodiment, an optical fiber 17 configured to guide therapeutic light based on laser light for performing a treatment is inserted into the treatment instrument channel 16, and a connector 17a on a back end of the optical fiber 17 extended outside of the treatment instrument insertion port 16a is detachably connected to the control apparatus 3.

Therapeutic light generated by the light source section 12 and guide light for visually checking an application position of the therapeutic light enter the back end of the optical fiber 17. The therapeutic light and the guide light are transmitted by a common optical fiber 17, and from a distal end surface of the optical fiber 17 protruded from a distal end opening of the treatment instrument channel 16, the therapeutic light and the guide light are emitted toward a front side facing the distal end surface at small beam diameters. An application region of the therapeutic light and an application region of the guide light applied from the distal end surface of the optical fiber 17 toward the subject 5 are substantially equal.

However, for example, a mask 25*f* is arranged on an optical path of the guide light as shown in FIG. 1 to block a central side of the guide light. Therefore, an application region Rg of the guide light shown in FIG. 4 and the like is an annular region in which a center side in a circular application region Rt of the therapeutic light is cut. The mask 25*f* may not be used, and the application region of the guide light may coincide with the circular application region of the therapeutic light.

Note that in the present endoscope apparatus 1, in order to check a position for applying (generating) the therapeutic light as described later, only the guide light is applied in some cases in a state that the therapeutic light is not applied. However, when the therapeutic light is applied, the guide light is also applied. Furthermore, a guide light source 24*d* described later has much smaller energy density (light quantity density) compared to the therapeutic light generated by a therapeutic light source 24*c*, and the guide light does not affect the application region in the subject 5 even if the guide light is continuously applied. Therefore, the application region based on the application of the guide light can be checked as the application region of the therapeutic light of the case that the therapeutic light is applied (not only when the therapeutic light is applied, but also when the therapeutic light is not applied).

In the present endoscope apparatus 1, the excitation light and the therapeutic light are set in a same wavelength band. Therefore, reflected light based on the therapeutic light is cut by the excitation light cut filter 15, and the CCD 14 does not generate an image based on the reflected light. On the other hand, a wavelength band of the guide light is set to a wavelength band for transmitting through the excitation light cut filter 15, and the CCD 14 picks up an image of reflected light from the subject side based on the guide light.

The CCD 14 is subjected to image processing by the image processing section (or image processing unit) 21 of the first embodiment provided in the control apparatus 3. The image processing section 21 outputs a generated image signal to the monitor 4, and the monitor 4 displays an image picked up by the CCD 14. Therefore, in the state that the therapeutic light is applied, the application position of the therapeutic light and the application region as a region of the application position (or application region as a region including a set of application positions) can be checked from the image based on the guide light displayed on the monitor 4.

The present endoscope apparatus 1 further includes: a light source control section (or light source control unit) 22 configured to control operation of the light source section 12; and an input apparatus (or input unit) 23 including a keyboard, a mouse, or the like for inputting an instruction to the light source control section 22 or the image processing section 21.

The input apparatus 23 includes: a mode selection switch SW1 for selecting an automatic control mode (or automatic mode) for automatically applying the therapeutic light based on an image pickup signal picked up by the CCD 14 and a manual mode for manually applying the therapeutic light; a therapeutic light switch SW2 for turning on and off the application of the therapeutic light; and a set value input section 23*a* for inputting a set value for stopping the application of the therapeutic light. Note that although the light source control section 22 is provided separately from the light source section 12 in the example illustrated in FIG. 1, the light source section 12 may include the light source control section 22.

In the present endoscope apparatus 1, after a fluorescent substance (or agent) that is easily accumulated on a lesion site (or lesion part) and that emits fluorescence when excitation light in a predetermined wavelength band is applied is administered to the subject 5, a treatment for curing the lesion site is performed by applying the therapeutic light.

In the present endoscope apparatus 1, a treatment method is performed based on PIT for performing a treatment by setting the excitation light and the therapeutic light to the same wavelength (band), and a fluorescent substance with an effect of eliminating the lesion tissue by applying the therapeutic light in the same wavelength band as the excitation light is adopted as the fluorescent subject. Therefore, the therapeutic light is applied to the lesion site on which the fluorescent substance is accumulated, and the therapeutic light has a function of effective light that acts to eliminate the lesion tissue.

As a result of the application of the therapeutic light, the lesion site on which the fluorescent substance is accumulated disappears (decreases) with an application time period of the therapeutic light. Therefore, the fluorescence image (information of the fluorescence image) can be monitored to figure out progression (or advancement) of the effect of the application of the therapeutic light on a living body (effect of eliminating the lesion site). As described later, a luminance ratio including the information of the progression of the effect is calculated and outputted to the display apparatus in the present embodiment, and a surgeon can refer to the information to accurately check the progression of the effect of the application of the therapeutic light.

The light source section 12 includes: an excitation light source 24*a* configured to generate excitation light in a predetermined wavelength band; a reference light source 24*b* configured to generate reference light; the therapeutic light source 24*c* configured to generate therapeutic light; and the guide light source 24*d* configured to generate guide light.

Figure 2A:
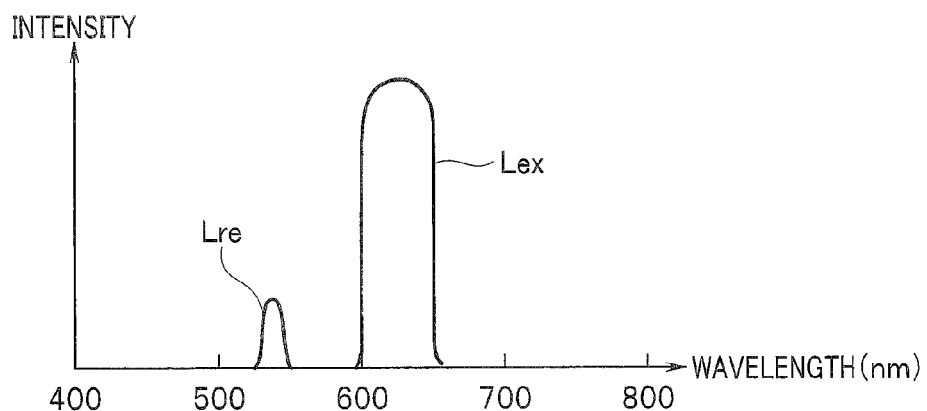
FIG. 2A is a diagram showing wavelengths and intensities of excitation light and reference light generated by an excitation light source and a reference light source, respectively.

FIG. 2A shows a characteristic Lex of wavelength band and intensity of the excitation light generated by the excitation light source 24*a* and a characteristic Lre of wavelength band and intensity of the reference light generated by the reference light source 24*b*. In the example shown in FIG. 2A, the wavelength band of the excitation light is set to 600 to 650 nm, and the wavelength band of the reference light is set to, for example, 530 to 550 nm belonging to a green wavelength band. By applying the excitation light to the subject 5 in the state that the fluorescent substance is administered, the fluorescent substance emits fluorescence in a wavelength band Lfl as shown in FIG. 2C.

Figure 2B:
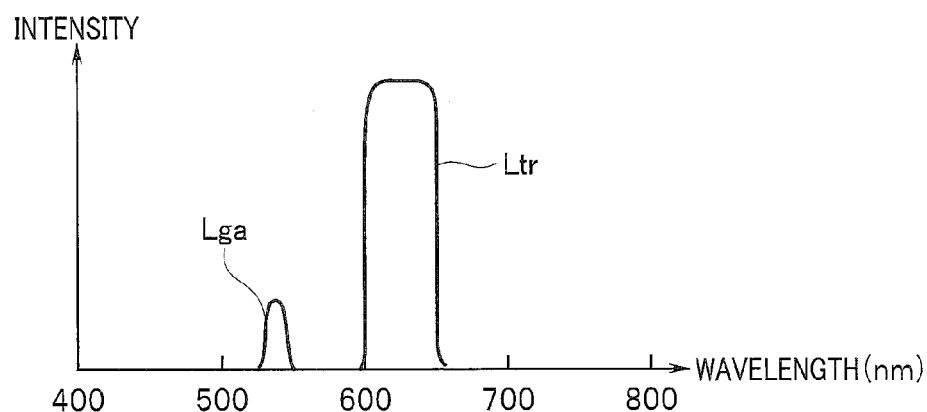
FIG. 2B is a diagram showing wavelengths and intensities of therapeutic light and guide light generated by a therapeutic light source and a guide light source, respectively.

FIG. 2B shows a characteristic Ltr of wavelength band and intensity of the therapeutic light generated by the therapeutic light source 24*c* and a characteristic Lga of wavelength band and intensity of the guide light generated by the guide light source 24*d*. In an example shown in FIG. 2B, the wavelength band of the therapeutic light is set to 600 to 650 nm that is the same as the wavelength band of the therapeutic light, and the wavelength band of the guide light is set to, for example, 530 to 550 nm belonging to, for example, a green wavelength band.

Figure 2C:
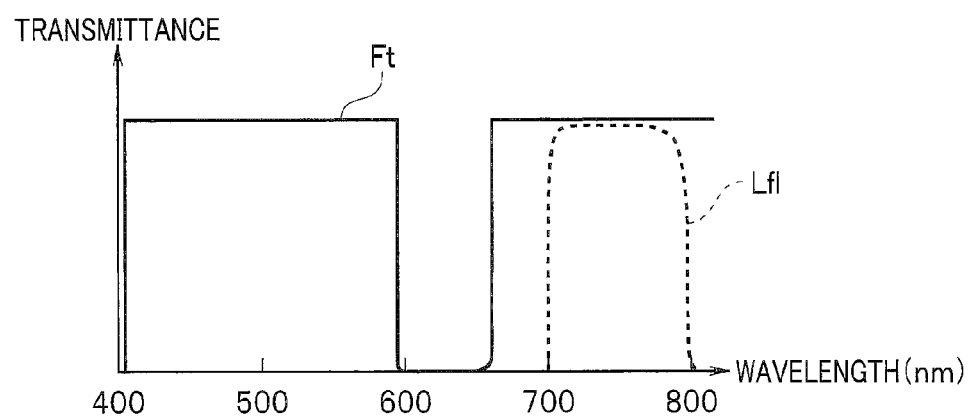
FIG. 2C is a diagram showing transmission characteristics of an excitation light cut filter with respect to the wavelength.

FIG. 2C shows a transmission characteristic Ft of the excitation light cut filter 15. As shown in FIG. 2C, the excitation light cut filter 15 is set to a characteristic in which, for example, 590 to 660 nm including the wavelength band of the excitation light and the wavelength band of the therapeutic light is cut, and the light transmits through the green (G) wavelength band and the wavelength band Lfl of the fluorescence generated by the fluorescent substance. In FIG. 2C, the excitation light cut filter 15 is set to a characteristic in which the light transmits through 400 to 590 nm and 660 to an infrared region over 800.

The CCD 14 is sensitive to a visible band and an infrared wavelength band including a wavelength band of the fluorescence on a long wavelength side of a red (R) wavelength band.

As shown in FIG. 1, the excitation light generated by the excitation light source 24a is reflected by a mirror 25a arranged on an opposing optical path. Excitation light in reflected light of the mirror 25a is selectively reflected based on selective reflection/transmission characteristics according to a wavelength of a dichroic mirror 25b arranged on an opposing optical path. The light enters a back end surface of the light guide 11 through a condensing lens 25c arranged on an optical path of the reflected light.

The reference light generated by the reference light source 24b enters the dichroic mirror 25b arranged on the opposing optical path, and the reference light is selectively transmitted by the dichroic mirror 25b. The reference light enters the back end surface of the light guide 11 through the condensing lens 25c arranged on the transmitted optical path. Note that since a monochrome image pickup device is used in the present endoscope apparatus 1, the light source control section 22 controls the excitation light source 24a and the reference light source 24b to frame-sequentially generate the excitation light and the reference light as described later, and the excitation light and the reference light are frame-sequentially applied toward the observation site in the subject 5.

The therapeutic light generated by the therapeutic light source 24c enters a dichroic mirror 25d arranged on an opposing optical path, and the therapeutic light is selectively transmitted by the dichroic mirror 25d. The therapeutic light enters a back end surface of the optical fiber 17 arranged on the transmitted optical path.

Figure 4A:
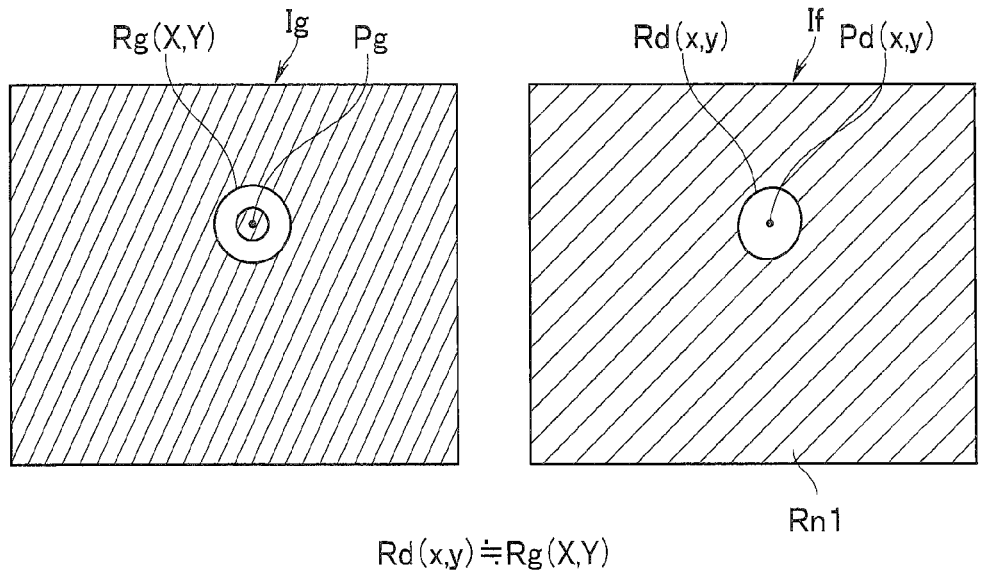
FIG. 4A is a diagram showing a guide light image and a fluorescence image in a state that an application region of the guide light almost coincides with a region of a lesion part in the fluorescence image.

The guide light generated by the guide light source 24d is reflected by a mirror 25e arranged on an opposing optical path. Reflected light of the mirror 25e is selectively reflected by the dichroic mirror 25d arranged on the opposing optical path, and the reflected light enters the back end surface of the optical fiber 17 arranged on the optical path of the reflected light. Note that the mask 25f for blocking the transmission through the circular central part is arranged on the optical path of the guide light. Therefore, the application region Rg of the guide light transmitted (guided) by the optical fiber 17 through the mask 25f and applied to the subject 5 is an annular region as shown in FIG. 4A and the like. The mask 25f may not be used. In this case, the application region Rg of the guide light is circular and coincides with the application region of the therapeutic light.

On the other hand, a CCD drive signal generated by a CCD drive circuit 31 in the image processing section 21 is applied, and the CCD 14 outputs a photoelectrically converted image pickup signal. The image pickup signal is inputted to a preprocessing circuit 32 in the image processing section 21. A correlated dual sampling circuit (abbreviated as CDS circuit) inside of the preprocessing circuit 32 extracts signal components in the image pickup signal, and the preprocessing circuit 32 outputs the signal components as an image signal to a multiplexer 33 after further performing A/D conversion and the like.

In this way, although the preprocessing circuit 32 in the image processing section 21 may be defined to execute preprocessing of converting the image pickup signal outputted from the CCD 14 into the image signal, the preprocessing circuit 32 in the image processing section 21 may be defined to output, to the multiplexer 33, the image pickup signal obtained by applying signal processing to the image pickup signal outputted from the CCD 14. They are just different in forms, and the contents are substantially the same. In the present specification, the former case will be mainly described.

An output end of the multiplexer 33 is connected to a memory section (or memory unit) 34 including three frame memories. A fluorescence memory 34a, a reference light memory 34b, and a guide light memory 34c as three frame memories forming the memory section 34 are connected to the multiplexer 33, and the multiplexer 33 frame-sequentially switches the three frame memories. Note that as described later, the multiplexer 33 frame-sequentially switches two frame memories in the state that the guide light is not applied.

Image signals stored in the three frame memories are inputted to a display control circuit 35. The display control circuit 35 generates a color image signal of a combined image Ic as an observed image obtained by allocating a fluorescence image If as an image of fluorescence, a reference light image Ir as an image of reference light, and a guide light image Ig as an image of guide light to different colors, respectively, and superimposing (combining) the images. The display control circuit 35 outputs the color image signal to the monitor 4. The monitor 4 performs a color display of the fluorescence image If, the reference light image Ir, and the guide light image Ig in which different colors are respectively allocated.

The guide light image Ig is a therapeutic light (application) position image including the application position of the therapeutic light. In other words, the therapeutic light position image (information) including the application position of the therapeutic light is a guide light image (information). Note that in the present specification, the fluorescence image, the guide light image, and the like have the same meanings as fluorescence image information, guide light image information, and the like.

The image processing section 21 of the present endoscope apparatus 1 includes a contrast calculation circuit 36 configured to calculate (or extract) a luminance value of the application region in the fluorescence image and a luminance value of a region other than the application region of the case that the therapeutic light is applied to the region of the lesion part and to calculate a ratio of the regions as described below. Note that as described later, in the calculation of the luminance value of the region other than the application region, part of the region (region of lesion part) is removed in some cases. In the calculation of the luminance value of the application region, part of the region (region of normal part) is also removed in some cases. Therefore, it can be stated that the contrast calculation circuit 36 calculates (or extracts) a luminance value corresponding to the application region and a luminance value corresponding to the region other than the application region.

The contrast calculation circuit 36 includes following two input ends Ta and Tb to substantially include an input section to which fluorescence image information and therapeutic light position image information are inputted. The contrast calculation circuit 36 includes: the input end Ta to which the fluorescence image is inputted from the fluorescence memory 34a; and the input end Tb to which the guide light image is inputted from the guide light memory 34c including the application position of the guide light (corresponding to the therapeutic light position image including the application position of the therapeutic light of the case that the therapeutic light is applied).

In the present endoscope apparatus, in a state that the guide light is continuously applied (after time tg of FIG. 5), the guide light image (components) is mixed with the fluorescence image stored in the fluorescence memory 34a. Therefore, the image processing section 21 includes a fluorescence image generation circuit 36a configured to generate the fluorescence image If by subtracting the guide light image Ig (read from the guide light memory 34c) from the fluorescence image read from the fluorescence memory 34a. The fluorescence image generation circuit 36a includes a subtraction circuit. Note that in the state that the guide light is not applied, the fluorescence memory 34a outputs the fluorescence image If not including the guide light image Ig. In this case, the guide light memory 34c outputs a guide light image that is 0. Therefore, the fluorescence image generation circuit 36a can output the fluorescence image If regardless of whether the guide light is applied.

The fluorescence image If outputted from the fluorescence image generation circuit 36a is inputted to a lesion region extraction circuit 36b configured to extract a region of a lesion part (in the fluorescence image If). The lesion region extraction circuit 36b extracts, as a region Rd of the lesion part, a region in which the luminance value in the fluorescence image If is equal to or greater than a threshold Vth. In other words, the lesion region extraction circuit 36b judges whether the region Rd of the lesion part exists in the fluorescence image If. Note that the lesion region extraction circuit 36b may include a threshold circuit 36c configured to output the threshold Vth.

The lesion region extraction circuit 36b sends, to the light source control section 22, an extraction result indicating the extraction of the region Rd of the lesion part or a judgement result indicating the judgement that the region Rd of the lesion part exists. The light source control section 22 controls the guide light source 24d to emit light at a timing of the time tg in FIG. 5. Note that the light source control section 22 controls the light emission of the excitation light source 24a, the reference light source 24b, and the guide light source 24d so that the light emission includes application periods or illumination periods in which only the guide light is applied as shown in FIG. 5.

In the state that the guide light is applied to the subject 5 as the guide light source 24d emits light, the light source control section 22 sends information of the application of the guide light to a guide position detection circuit 36d of the image processing section 21. The guide position detection circuit 36d detects the application region Rg provided with the guide light and an application position Pg of the guide light as a center position of the application region Rg from the guide light image Ig outputted from the guide light memory 34c.

Note that the guide position detection circuit 36d may automatically start the operation of detecting the application position Rg (and the application position Pg) of the guide light after the extraction result indicating that the region Rd of the lesion part is extracted by the lesion region extraction circuit 36b.

The guide position detection circuit 36d also judges whether the application position Pg of the guide light is in the region Rd of the lesion part extracted by the lesion region extraction circuit 36b (has a function of a judgement circuit).

FIG. 4A shows an explanatory diagram of the operation of the guide position detection circuit 36d. FIG. 4A shows the fluorescence image If outputted from the fluorescence image generation circuit 36a and the guide light image Ig outputted from the guide light memory 34c (after the time tg of the application of the guide light and before a time tt in which the therapeutic light is not applied).

A region indicated in white in the fluorescence image If shows the region Rd (x, y) of the lesion part with the luminance value equal to or greater than the threshold Vth, and the region has a luminance value higher than a region Rn1 of a normal part indicated by oblique lines outside of the region Rd (x, y) of the lesion part. Note that (x, y) represents coordinates of the region Rd of the lesion part indicated in white in the fluorescence image If. The notation of (x, y) will be usually omitted, and for example, the region is indicated by the region Rd of the lesion part.

The white annular region Rg (X, Y) in the guide light image Ig indicates a region provided with beam-like guide light, and the luminance value is much higher than a surrounding region indicated by oblique lines not provided with the guide light. In FIG. 4A, the smaller the pitches between oblique lines in the oblique lines, the closer the luminance value to 0.

As described, the circular region with a combination of the annular application region Rg of the guide light and the region with a low luminance value on the center side coincides with the application region Rt of the case that the therapeutic light is applied. Therefore, as described below, the guide position detection circuit 36d can have a function of an application position specification circuit configured to specify the application region Rt (and application position Pt) of the therapeutic light in addition to the function of detecting the application region Rg and the application position Pg of the guide light. Although the region of the application position Pt is the application region Rt in the case of the therapeutic light, the center position or the center of gravity position of the application region Rt may be defined as the application position Pt as in the case of the guide light.

To detect the application region Rg provided with the guide light in the guide light image Ig, the guide position detection circuit 36d detects a region with a luminance value equal to or greater than the threshold (of a threshold circuit 36e) Vtg as the application region Rg (X, Y) of the guide light. Note that (X, Y) represents coordinates of the white annular region in the guide light image Ig, and the notation of (X, Y) will be usually omitted.

The guide position detection circuit 36d sets a center position of the application region Rg (X, Y) as the application position Pg of the guide light and determines whether the application position Pg exists near a center position or a center of gravity position Pd (X, Y) of the region Rd of the lesion part. For example, the guide position detection circuit 36d has a function of a judgement circuit 36f configured to judge whether a condition Rd (x, y)≈Rg (X, Y) is satisfied within an error of a small value δ. Note that in FIG. 4A, Rd (x, y)≈Rg (X, Y) is satisfied.

If the judgement circuit 36f judges that the condition is satisfied, the judgement circuit 36f sends information of the judgement result to the light source control section 22, and the light source control section 22 controls the therapeutic light source 24c to emit light at the timing of the time if in FIG. 5.

After the time tt in which the therapeutic light is applied, the guide position detection circuit 36d has a function of an application position specification circuit (or application region specification circuit) 36g configured to specify the application region Rt and the application position Pt of the therapeutic light from the application region Rg of the guide light. Although the guide position detection circuit 36d has the function of the application position specification circuit 36g in FIG. 3, the application position specification circuit 36g may be included outside of the guide position detection circuit 36d.

For the application region Rt and the application position Pt of the therapeutic light in the state that the therapeutic light is applied, the guide position detection circuit 36d (the application position specification circuit 36g of the guide position detection circuit 36d) substitutes a circular shape for the annular ring in the annular application region Rg and application position Pg of the guide light to thereby specify the application region Rt and the application position Pt. That is, the annular application region Rg is converted to the circular application region Rt, and the application position Pg is specified as the application position Pt. However, the specification is performed on the fluorescence image If (or performed for the fluorescence image If).

Figure 4B:
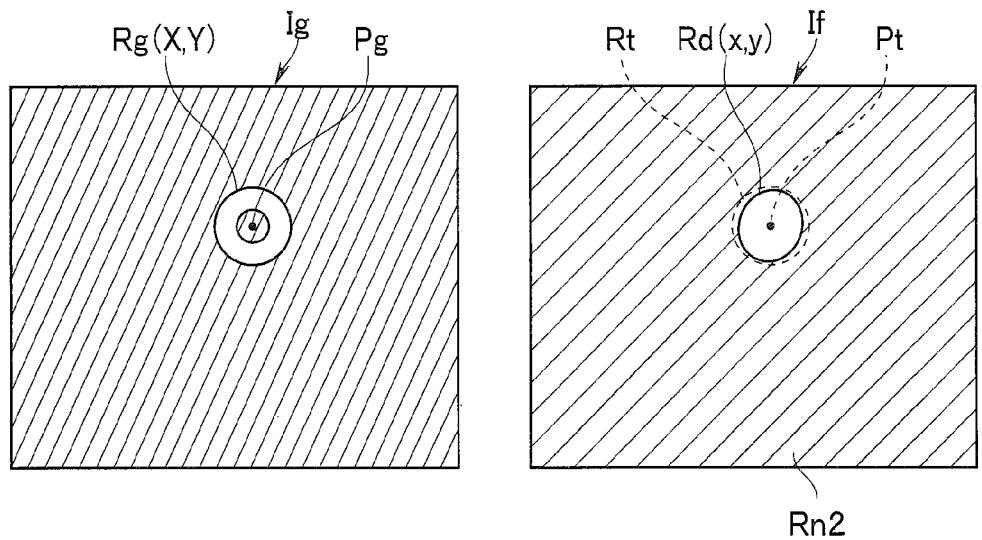
FIG. 4B is a diagram showing a guide light image and a fluorescence image in a state that the therapeutic light is applied.

FIG. 4B shows the fluorescence image If and the guide light image Ig in the state that the therapeutic light is applied. The guide light image Ig is in the same state as the guide light image Ig of FIG. 4A.

On the other hand, the fluorescence image If is a fluorescence image If in the state that the therapeutic light is not applied in FIG. 4A, and the region Rt of the lesion part with a high luminance value is indicated in white. In the fluorescence image If in FIG. 4B, the application region Rt of the therapeutic light is further indicated by a dotted line. Note that the application region Rt of the therapeutic light indicated by the dotted line in FIG. 4B is for the description, and the luminance value in the fluorescence image If (components) is not increased.

The guide position detection circuit 36d (the application position specification circuit 36g of the guide position detection circuit 36d) specifies, as a non-application region Rn2, a region not provided with the therapeutic light on the outside of the application region Rt. In this case, the application position specification circuit 36g may extract, as the non-application region Rn2, a region with a luminance value lower than an average luminance value of the application region Rt (or an average luminance value of the region Rd of the lesion part included in the application region Rt) by a predetermined value or more.

In the case described in the present embodiment, the application region Rt of the therapeutic light has a size covering the region Rd of the lesion part as shown in FIG. 4B. In other words, the application region Rt of the therapeutic light is set for the region Rd of the lesion part to substantially cover the region Rd, and the treatment is performed by the application of the therapeutic light in the image processing of the present embodiment.

Therefore, the non-application region Rn2 on the outside of the application region Rt of the therapeutic light is substantially equal to the region Rn1 of the normal part. Note that a case in which the application region Rt of the therapeutic light is much larger than the region Rd of the lesion part and a case with a plurality of regions of lesion part will be described later.

The application position specification circuit 36g outputs the information of the specified application region Rt and non-application region Rn2 to an average luminance calculation circuit 36h. The average luminance calculation circuit 36h calculates an average luminance value Btav of the application region Rt and an average luminance value Bnav of the non-application region Rn2 and outputs the values to a luminance ratio calculation circuit 36i.

The luminance ratio calculation circuit 36i calculates a TBR value (tumor background ratio value, hereinafter abbreviated as TBR) as a ratio Btav/Bnav of the average luminance value Btav and the average luminance value Bnav and outputs it (calculated ratio TBR) as information of progression to the display control circuit 35. Note that the TBR is equivalent to a definition of a ratio of a luminance that is a fluorescence high luminance in a region of a lesion part to a luminance that is a fluorescence low luminance in a region of a surrounding normal part (background part).

Figure 3:
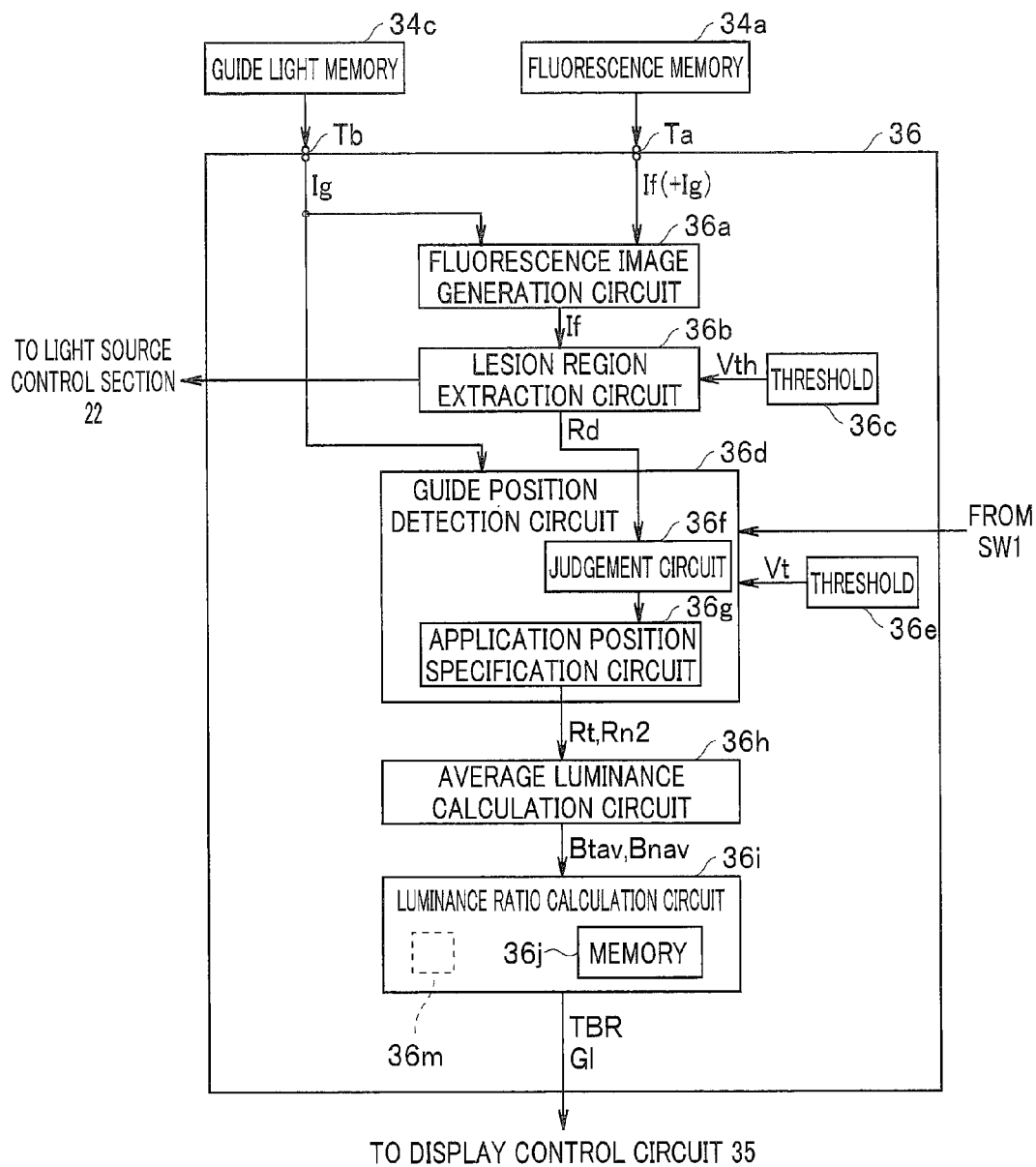
FIG. 3 is a block diagram showing a configuration of a contrast calculation circuit.

As shown in FIG. 3, the luminance ratio calculation circuit 36i may chronologically store the data of the calculated luminance ratio in a memory 36j inside of the luminance ratio calculation circuit 36i in association with time periods and may output the data of the chronologically (temporally) changing luminance ratio stored in the memory 36j to the display control circuit 35.

The TBR as a luminance ratio calculated by the luminance ratio calculation circuit 36i is a value obtained by dividing the average luminance value Btav in the application region Rt provided with the therapeutic light (in the fluorescence image) by the average luminance value Bnav of the non-application region Rn2 (that can be assumed as the region Rn1 of the normal part). Therefore, the value of the TBR is information indicating the progression of the effect when the therapeutic light is applied (to the lesion part). Note that a prediction circuit 36m may be provided as indicated by a dotted line in FIG. 3. As described later, the prediction circuit 36m executes a process of predicting values of the TBR in times after a current time based on a plurality of already calculated values of TBR and predicting (calculating) a time tpr that the value reaches a set value.

In the present embodiment, the TBR that is the luminance ratio of both regions is calculated. Therefore, a change in the value of the TBR can be suppressed even if, for example, the luminance value (average) of the application region Rt applied to cover the region Rd of the lesion part and the luminance value (average) of the non-application region Rn2 formed in the region Rn1 of the surrounding normal part change, depending on a distance between the region Rd of the lesion part and the CCD 14 arranged on the distal end portion of the insertion portion 6.

Although the region of the lesion part in which the fluorescent substance is accumulated has a large luminance value (compared to the luminance value of the region of the normal part) in the state that the therapeutic light is not applied, the value changes to smaller luminance values along with the elimination of the lesion tissue of the lesion part after the application of the therapeutic light.

Therefore, the luminance value of the application region Rt on the basis of the luminance value of the region of the normal part will be information indicating the progression of the effect of the application of the therapeutic light.

In the present embodiment, in addition to the output of the information of the TBR as a luminance ratio, luminance ratio change information as information indicating a temporal change in the TBR stored in the memory 36j is generated, and the luminance ratio change information is outputted to the monitor 4 as a display apparatus through the display control circuit 35. The memory 36j forms an output section configured to output the information regarding the progression of the effect when the therapeutic light is applied to a living body, based on the TBR calculated by the luminance ratio calculation circuit 36i.

Note that time information at the start of the application of the therapeutic light is stored in a control circuit 37, the memory 36j in the contrast calculation circuit 36, or the like from the light source control section 22. In generating the information indicating the temporal change in the TBR, the start of the application of the therapeutic light is set as 0, and information of the TBR corresponding to a lapse of time period is generated.

The display control circuit 35 separates and generates a fluorescence image signal of the fluorescence image If, a reference light image signal of the reference light image Ir, and a guide light image signal of the guide light image Ig from the image signals outputted from the fluorescence memory 34a, the reference light memory 34b, and the guide light memory 34c included in the memory section 34 and outputs the signals to channels R, G, and B of the monitor 4.

Note that the fluorescence image signal outputted from the fluorescence memory 34a is a fluorescence image signal in which the guide light image Ig is mixed as described above, and the subtraction circuit 35a in the display control circuit 35 generates the fluorescence image signal (like the fluorescence image generation circuit 36a). However, in place of the fluorescence image signal outputted from the fluorescence memory 34a, the fluorescence image signal generated by the fluorescence image generation circuit 36a may be inputted to the display control circuit 35. In this case, the subtraction circuit 35a in the display control circuit 35 is not necessary.

The monitor 4 displays in colors, in three primary colors, the fluorescence image signal of the fluorescence image If, the reference light image signal of the reference light image Ir, and the guide light image signal of the guide light image Ig inputted to the channels R, G, and B. Note that in FIG. 1, the images are indicated by the fluorescence image If, the reference light image Ir, and the guide light image Ig corresponding to the image signals inputted to the R, G, and B channels, respectively.

The data of the TBR as a temporally changing luminance ratio stored in the memory 36j is inputted to the display control circuit 35 from the luminance ratio calculation circuit 36i, and the data of the luminance ratio is added to the image signal and outputted to the monitor 4. As shown for example in FIG. 6A, the monitor 4 displays, in an image display area 4a, the combined image Ic obtained by combining colors of the fluorescence image If, the reference light image Ir, and the guide light image Ig and displays a graph G1 indicating the temporal change in the luminance ratio in a luminance ratio information display area 4b adjacent to the image display area 4a.

The display control circuit 35 also outputs, to the monitor 4, the data of the current luminance ratio outputted from the luminance ratio calculation circuit 36i. As shown for example in FIG. 6A, the monitor 4 displays the TBR (or TBR value) as the current luminance ratio in an area on an upper side of the luminance ratio information display area 4b.

The surgeon can observe the graph G1 indicating the temporal change in the luminance ratio displayed on the monitor 4 to figure out a situation of a reduction in the fluorescence luminance value of the region Rd of the lesion part after the application of the therapeutic light (progression of the effect of the application of the therapeutic light), and the surgeon can easily figure out the timing for stopping the application of the therapeutic light.

Figure 6A:
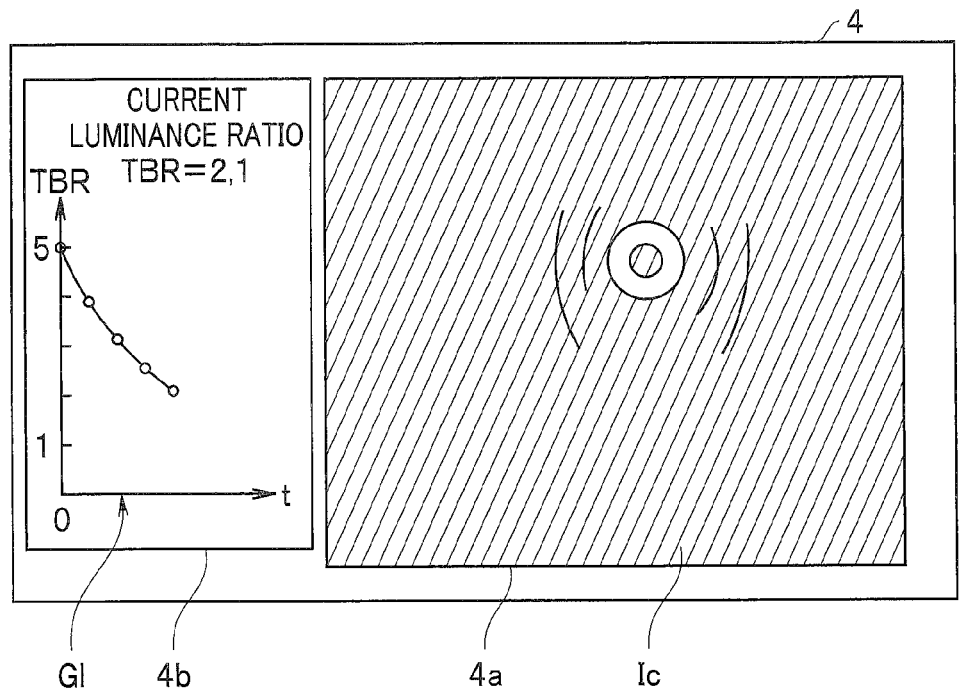
FIG. 6A is a diagram showing a combined image of the fluorescence image, a reference light image, and the guide light image and information of a luminance ratio displayed on a monitor.
Figure 6B:
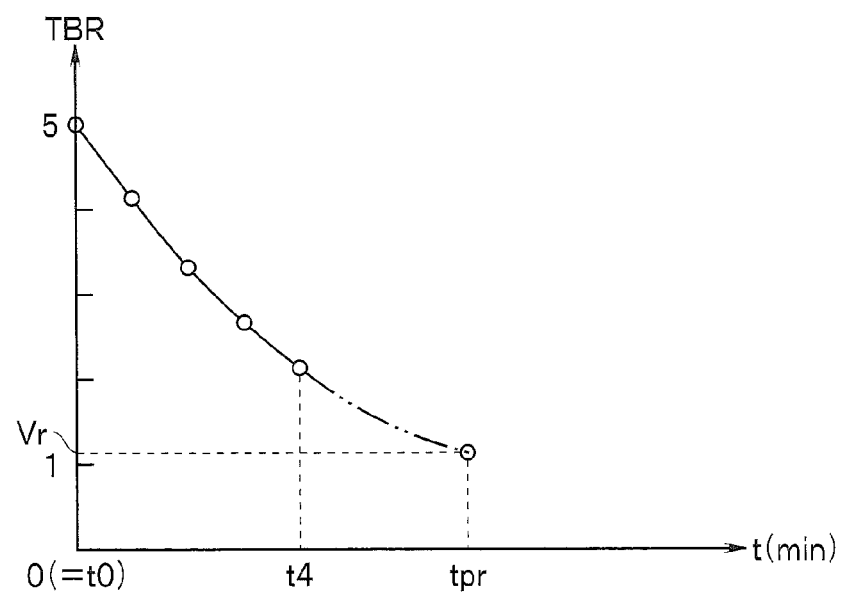
FIG. 6B is a diagram showing a graph of a temporal change in TBR as a luminance ratio.

FIG. 6B shows an expanded graph G1 of FIG. 6A. In FIG. 6B, the time of the start of the application of the therapeutic light is 0, and a curve of the TBR plotting the TBR calculated at, for example, predetermined time intervals is illustrated. FIG. 6B shows a situation that the TBR is calculated at times 0 (=t0) to t4.

Note that an automatic mode in which the light source control section 22 automatically applies the therapeutic light based on the judgement result of the judgement circuit 36f is described in the case described above. That is, the mode selection switch SW1 is provided on the input apparatus 23 of FIG. 1, and when the automatic mode is turned on (selected) by the mode selection switch SW1, the operation is performed as described above. On the other hand, when the mode selection switch SW1 is turned off, the manual mode is set. In this case, the surgeon manually performs operation of turning on the therapeutic light switch SW2 provided on the input apparatus 23, and the light source control section 22 applies the therapeutic light.

The image processing section 21 includes the control circuit 37 configured to control the CCD drive circuit 31, the preprocessing circuit 32, the multiplexer 33, the memory section 34, and the like. The control circuit 37 is connected to the light source control section 22 through a signal line and is capable of performing control operation in conjunction with control by one of them.

For example, in an initial state in which the endoscope apparatus 1 enters the operation state (as described later), the light source section 12 operates in a fluorescence observation mode for alternately generating the excitation light and the reference light and not generating the therapeutic light and the guide light. In this state, the control circuit 37 executes image processing of generating the fluorescence image and the reference light image.

In this case, the control circuit 37 controls the multiplexer 33 to switch the fluorescence memory 34a and the reference light memory 34b as two frame memories in the memory section 34 (to store the fluorescence image in the fluorescence memory 34a and store the reference light image in the reference light memory 34b).

When the fluorescent substance is accumulated on the lesion site, and the region Rd of the lesion part in which the luminance value of fluorescence equal to or greater than the threshold Vth is detected is detected, the state enters a state in which the guide light is applied to check the application position. After the position check, the state switches to a state in which the therapeutic light is applied to perform the treatment.

In the state that the therapeutic light is applied, the contrast calculation circuit 36 specifies the application region Rt and the non-application region Rn2 of the therapeutic light and calculates average luminance values of the respective regions. The contrast calculation circuit 36 further calculates the RTB as a luminance ratio, and the monitor 4 displays the graph G1 of the temporal change of the RTB along with the combined image.

Note that the calculation of the TBR as a luminance ratio and the display of the calculated TBR may be performed all the time or may be performed at certain time intervals. For example, the time intervals for calculating the TBR may be able to be set by inputting instruction data of the time intervals for calculating the TBR from the set value input section 23a in the input apparatus 23 (or an instruction value input section difference from the set value input section 23a). The calculation of the TBR as a luminance ratio and the timing of updating the display of the calculated TBR may be performed according to user setting inputted from the input apparatus 23 or may be automatically set based on the change in the curve of the temporally changing TBR. The fluorescence image generation circuit 36a, the lesion region extraction circuit 36b, the threshold circuit 36c, the guide position detection circuit 36d, the threshold circuit 36e, the judgement circuit 36f, the application position specification circuit 36g, the average luminance calculation circuit 36h, and the luminance ratio calculation circuit 36i included in the contrast calculation circuit 36 may be formed by using hardware, such as dedicated electronic circuits, or may be formed by software by using a central processing unit (CPU).

The image processing section 21 of the first embodiment forming the image processing apparatus includes: the input ends Ta and Tb forming an input section configured to receive fluorescence image information obtained by picking up an image of fluorescence from the subject 5 provided with a fluorescent substance that is accumulated on a lesion site, the fluorescent substance emitting fluorescence after application of light in an excitation wavelength and acting on a living body after the application of the light in the excitation wavelength, and receive therapeutic light position image information (guide light image Ig information corresponding to the therapeutic light position image information) including an application position of therapeutic light for causing the fluorescent substance to act on the living body; the application position specification circuit 36g forming a specification section configured to specify an application region as a region of the application position of the therapeutic light in the fluorescence image information from the therapeutic light position image information inputted to the input section; the average luminance calculation circuit 36h forming an extraction section configured to extract an average luminance value as a luminance value corresponding to the application region of the therapeutic light specified by the specification section in the fluorescence image information inputted to the input section and an average luminance value as a luminance value corresponding to a region other than the application region in the fluorescence image information; and the luminance ratio calculation circuit 36i forming a calculation section configured to calculate and output a ratio of the luminance value corresponding to the application region extracted by the extraction section to the luminance value corresponding to the region other than the application region.

Figure 7:
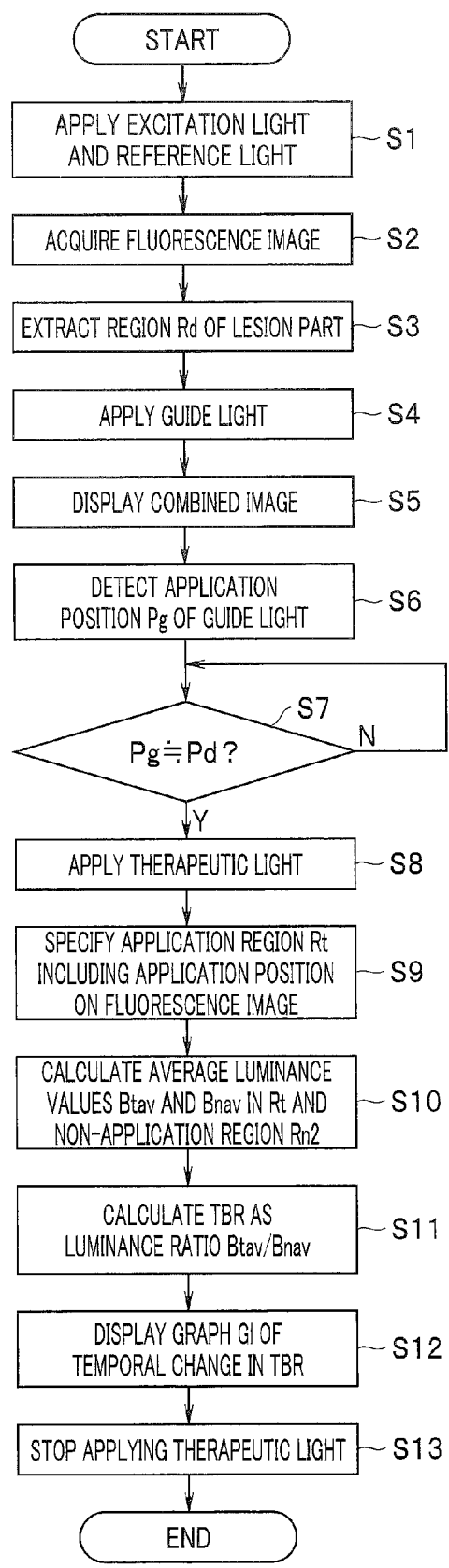
FIG. 7 is a flowchart showing content of operation of the endoscope apparatus provided with the first embodiment.

Next, an effect of the endoscope apparatus 1 including the image processing section 21 of the present embodiment will be described. FIG. 7 shows a representative process by the endoscope apparatus 1.

A fluorescent substance corresponding to the treatment method of PIT is administered in advance to the subject 5. After the administration of the fluorescent substance, the endoscope apparatus 1 set as shown in FIG. 1 observes an observation site, such as a diseased part, in the subject 5 after a lapse of time period in a level that the fluorescent substance accumulates on the lesion site.

In step S1 of FIG. 7, the light source control section 22 controls the excitation light source 24a and the reference light source 24b to emit light. Consequently, the excitation light source 24a and the reference light source 24b frame-sequentially generate the excitation light and the reference light, respectively, as shown in FIG. 5. The generated excitation light and reference light are transmitted by the light guide 11. The excitation light and the reference light are spread from the distal end surface of the light guide 11 and applied toward the observation site.

In FIG. 5, T denotes one frame period. For example, the excitation light is applied in one frame period T that is a first timing, and the CCD 14 acquires (picks up) a fluorescence image emitted from the fluorescent substance administered to the subject 5 as a result of the application of the excitation light in the one frame period T.

In a next one frame period T at a second timing in which the excitation light is turned off (OFF), the reference light is applied in an illumination period Tr shorter than the one frame period T. In this way, the reference light can be applied only in the illumination period Tr shorter than the one frame period T to adjust, at a proper level, the luminance level of the fluorescence image of the case that the image is picked up based on the fluorescence and the luminance level of the reference light image acquired by the application of the reference light.

As described, the CCD 14 (forming the image pickup section) frame-sequentially picks up the fluorescence image emitted from the observation site side at the application of the excitation light and the reference light image reflected by the observation site side at the application of the reference light and outputs the frame-sequentially picked up fluorescence image pickup signal and reference light image pickup signal to the image processing section 21. In the image processing section 21, the preprocessing circuit 32 executes the process of converting the fluorescence image pickup signal and the reference light image pickup signal to the fluorescence image signal and the reference light image signal.

The fluorescence image signal and the reference light image signal are stored in the fluorescence memory 34a and the reference light memory 34b, respectively. That is, as shown in step S2, the fluorescence memory 34a in the image processing section 21 acquires the fluorescence image.

Note that the fluorescence memory 34a and the reference light memory 34b function as an R channel image memory and a B channel image memory when the image is displayed in colors on the monitor 4. The fluorescence image If and the reference light image Ir are respectively combined in different colors and displayed on the monitor 4.

The fluorescence image acquired by the fluorescence memory 34a is inputted to the lesion region extraction circuit 36b through the fluorescence image generation circuit 36a in the contrast calculation circuit 36.

In step S3, the lesion region extraction circuit 36b compares the luminance value and the threshold Vth and extracts the region Rd of the lesion part with the luminance value equal to or greater than the threshold Vth in the fluorescence image If. In step S4 after the extraction of the region Rd of the lesion part, the light source control section 22 causes the guide light source 24d to emit light, and the emitted guide light is applied toward the diseased part from the distal end of the optical fiber 17. Note that as shown in FIG. 5, the guide light source 24d generates the guide light in the time tg.

When the guide light is applied, the light source control section 22 sends the information indicating the light emission of the guide light source 24d to the control circuit 37. The control circuit 37 performs control to execute a process of generating the guide light image in addition to the fluorescence image and the reference light image according to the light emission of the three light sources.

More specifically, the control circuit 37 controls the multiplexer 33 to sequentially switch the fluorescence memory 34a, the reference light memory 34b, and the guide light memory 34c as the three frame memories in the memory section 34 (to store the fluorescence image in the fluorescence memory 34a, store the reference light image in the reference light memory 34b, and store the guide light image in the guide light memory 34c).

The fluorescence image If+Ig stored in the fluorescence memory 34a of the memory section 34, the reference light image Ir stored in the reference light memory 34b, and the guide light image Ig stored in the guide light memory 34c are simultaneously read and outputted to the monitor 4 through the display control circuit 35.

As shown in step S5, the monitor 4 displays the combined image Ic obtained by combining the fluorescence image If, the reference light image Ir, and the guide light image Ig in colors of R, G, and B, respectively.

In step S6, the guide position detection circuit 36d detects the application region Rg of the guide light with the luminance value equal to or greater than the threshold Vt from the guide light image Ig as shown in FIG. 4A. The guide position detection circuit 36d also detects the application position Pg of the guide light.

In step S7, the judgement circuit 36f of the guide position detection circuit 36d judges whether the center of gravity position (or center position) Pd of the region Rd of the lesion part coincides with the center position of the application region Rg of the guide light that is the application position Pg within an error of a small value δ and waits until they coincide. The surgeon sets the positions such as by moving the distal end portion of the endoscope 2 to bring the positions to coincide with each other.

If the judgement circuit 36f judges that they coincide, the light source control section 22 automatically (in the case of the automatic mode) causes the therapeutic light source 24c to emit light as shown in step S8, and the therapeutic light is applied from the distal end of the optical fiber 17 toward the diseased part along with the guide light. Note that as shown in FIG. 5, the therapeutic light source 24c generates the therapeutic light at the time tt.

In next step S9, the application position specification circuit 36g specifies the application region Rt as a region of the application position Pt of the therapeutic light in the fluorescence image If from the fluorescence image If (in the state that the region Rd of the lesion part is detected) and the guide light image Ig (in the state that the application region Rg of the guide light is detected) as described in FIG. 4B. The application position specification circuit 36g outputs the specified application region Rt of the therapeutic light and the non-application region Rn2 outside of the application region Rt to the average luminance calculation circuit 36h.

In next step S10, the average luminance calculation circuit 36h calculates the respective average luminance values Btav and Bnav in the application region Rt and the non-application region Rn2 in the fluorescence image and outputs the average luminance values Btav and Bnav to the luminance ratio calculation circuit 36i.

In next step S11, the luminance ratio calculation circuit 36i calculates the TBR (=Btav/Bnav) that is a luminance ratio of the average luminance values Btav and Bnav in the application region Rt and the non-application region Rn2 and outputs the TBR to the monitor 4 through the display control circuit 35. The luminance ratio calculation circuit 36i adds the time information to the TBR by setting the time of the start of the application of the therapeutic light as 0 and memorizes the TBR in the memory 36j.

In next step S12, the luminance ratio calculation circuit 36i outputs the image data of the graph G1 of TBR that is the information indicating the temporal change in the TBR that is the luminance ratio stored in the memory 36j to the monitor 4 through the display control circuit 35. The monitor 4 displays the graph G1 of the temporally changing TBR as shown in FIG. 6A.

The surgeon can observe the graph G1 of the TBR to accurately check the progression of the effect of reducing the level of the lesion that is an effect of the application of the therapeutic light. The surgeon can also accurately figure out the time for stopping the application of the therapeutic light based on the tendency of the decrease in the value of the TBR with a lapse of time.

At the timing that the value of the TBR has become a value that does not require the application of the therapeutic light, the surgeon turns off the therapeutic light switch SW2 to stop the application of the therapeutic light as shown in step S13.

As a result of the stop of the application of the therapeutic light, the treatment based on the therapeutic light ends. The surgeon also stops the application of the guide light and extracts the endoscope from the subject 5 to end the process of FIG. 7.

Note that as described below, the surgeon may input (set) in advance a set value as a predetermined TBR value for stopping the application of the therapeutic light, and the luminance ratio calculation circuit 36i may automatically stop the application of the therapeutic light through the light source control section 22 if the calculated value of TBR becomes the predetermined TBR value.

Figure 8:
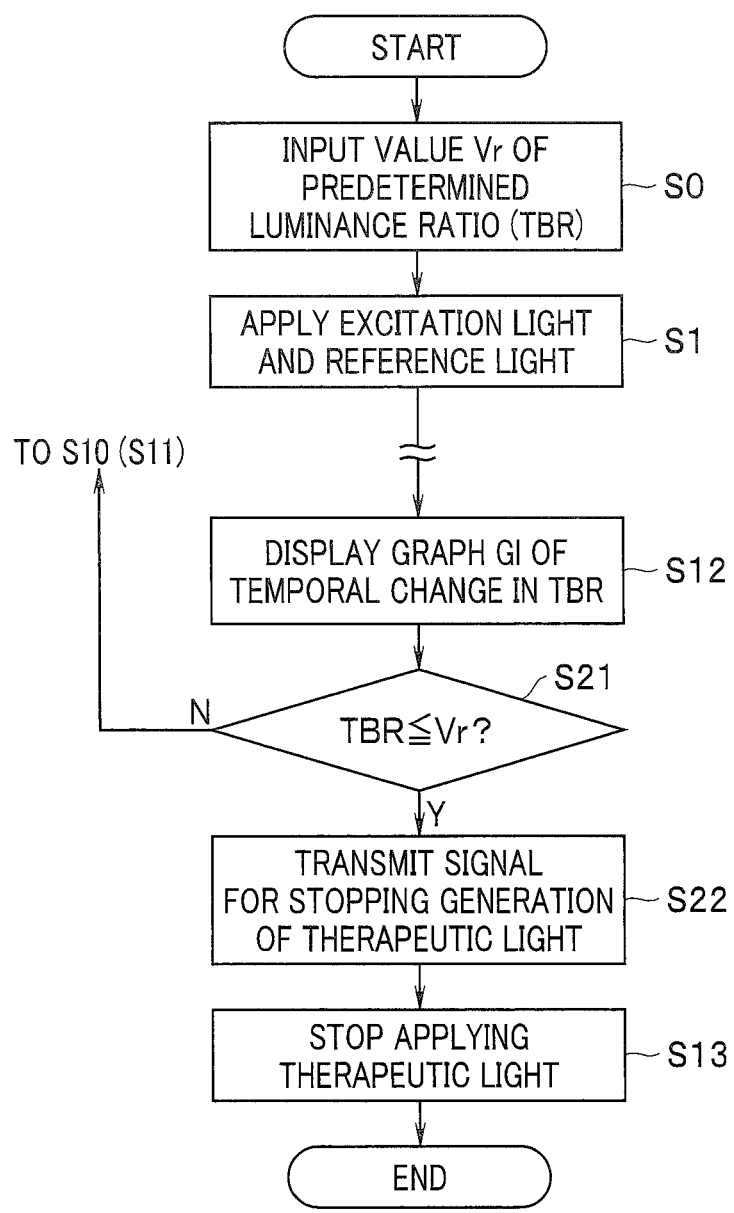
FIG. 8 is a flowchart showing a process of stopping application of the therapeutic light when the calculated luminance ratio reaches a predetermined value Vr.

FIG. 8 shows a process in this case. In this case, for example, the surgeon inputs a predetermined value of TBR Vr as a set value for stopping the application of the therapeutic light from a keyboard, a numeric keypad, or the like included in the input apparatus 23 in first step S0. The input apparatus 23 in this case forms the set value input section (or set value input apparatus) 23a configured to receive the set value.

The set value is stored in, for example, the memory 36j. Subsequently, the process of steps S1 to S12 shown in FIG. 7 is executed. After the process of step S12, the luminance ratio calculation circuit 36i compares and judges whether the calculated TBR has become equal to or smaller than the predetermined value of TBR Vr in step S21. If a judgement result indicates that the calculated TBR does not become equal to or smaller than the predetermined value of TBR Vr, the process returns to step S10 or step S11.

On the other hand, if the judgement result indicates that the calculated TBR is equal to or smaller than the predetermined value of TBR Vr, the luminance ratio calculation circuit 36i sends a signal for stopping the generation of the therapeutic light to the light source control section 22 included in the control section as shown in step S22. As shown in step S13, the light source control section 22 stops the generation of the therapeutic light, and the application of the therapeutic light stops. Although the generation or application of the therapeutic light is automatically stopped if the calculated TBR reaches the predetermined value of TBR Vr in the example shown in FIG. 8, a notification may be sent to a user, such as a surgeon, through sound or display.

According to the present embodiment with the operation, the progression of the effect of the application of the therapeutic light can be accurately checked. The temporal change in the TBR as a luminance ratio is displayed as the graph G1. Therefore, the progression of the effect of the application of the therapeutic light can be more accurately checked, and the time for stopping the application of the therapeutic light can be accurately figured out from the tendency of the temporal change in the TBR (excessive application of the therapeutic light or a lack of therapeutic light application can be prevented).

Although the case with one region of the lesion part described in the first embodiment, an image processing section 21B of a case with a plurality of discrete regions of the lesion part will be described in a first modification.

In a case with a plurality of discrete regions of the lesion part, a region of the lesion part where the therapeutic light is not applied exists in the non-application region Rn2 if the therapeutic light is applied to cover one region of the lesion part. Therefore, such a region can be removed to calculate the TBR as a luminance ratio to accurately check the progression of the effect of the application of the therapeutic light.

Figure 9:
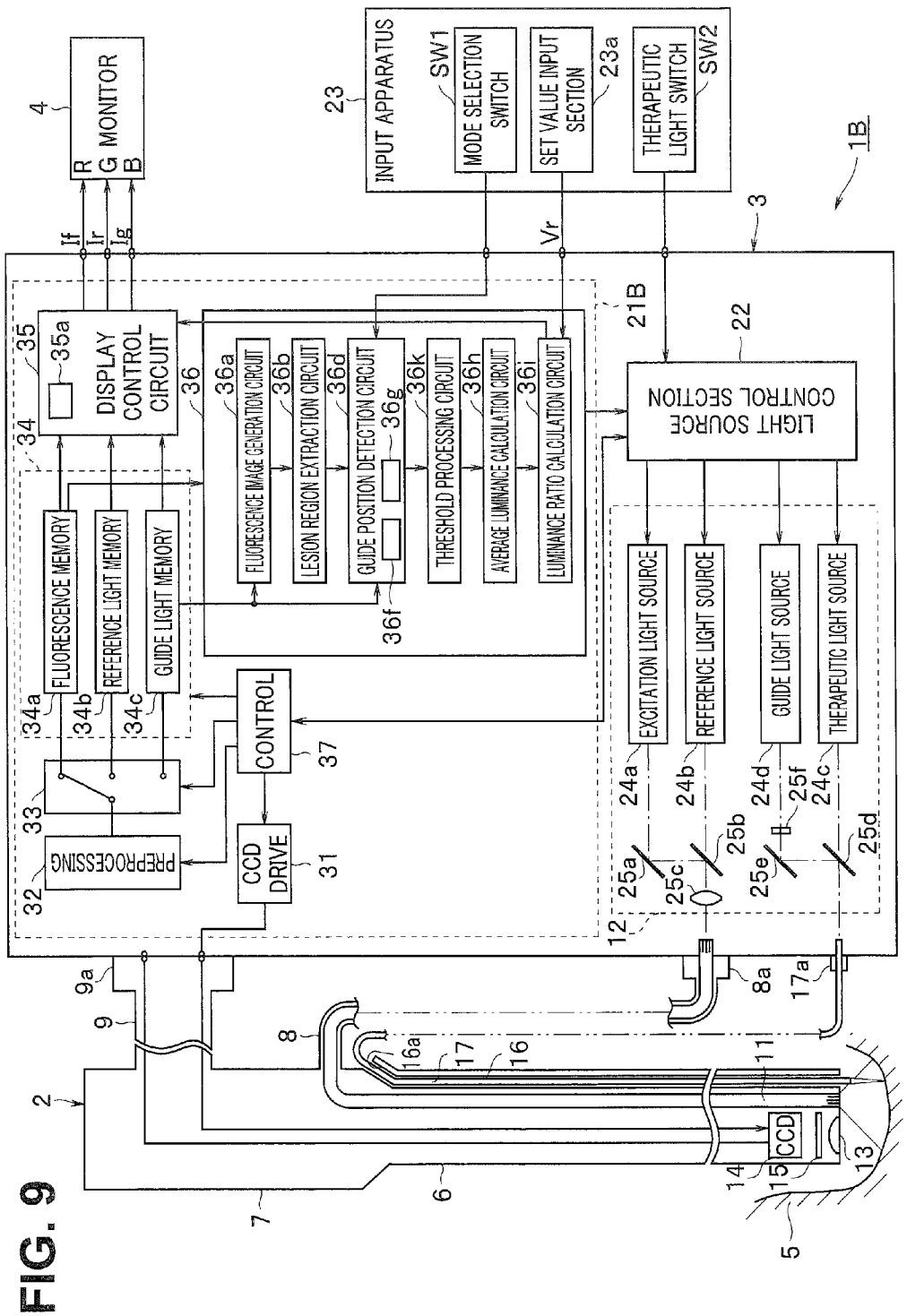
FIG. 9 is a diagram showing a configuration of an endoscope apparatus provided with a modification of the first embodiment.

FIG. 9 shows a configuration of an endoscope apparatus 1B including the image processing section 21B of the first modification. The endoscope apparatus 1B includes the image processing section 21B including the contrast calculation circuit 36 in which a threshold processing circuit 36k configured to execute threshold processing for the non-application region of the therapeutic light (on the fluorescence image If) is provided between the application position specification circuit 36g and the average luminance calculation circuit 36h on the contrast calculation circuit 36 in the image processing section 21 of the endoscope apparatus 1 of FIG. 1.

Figure 10:
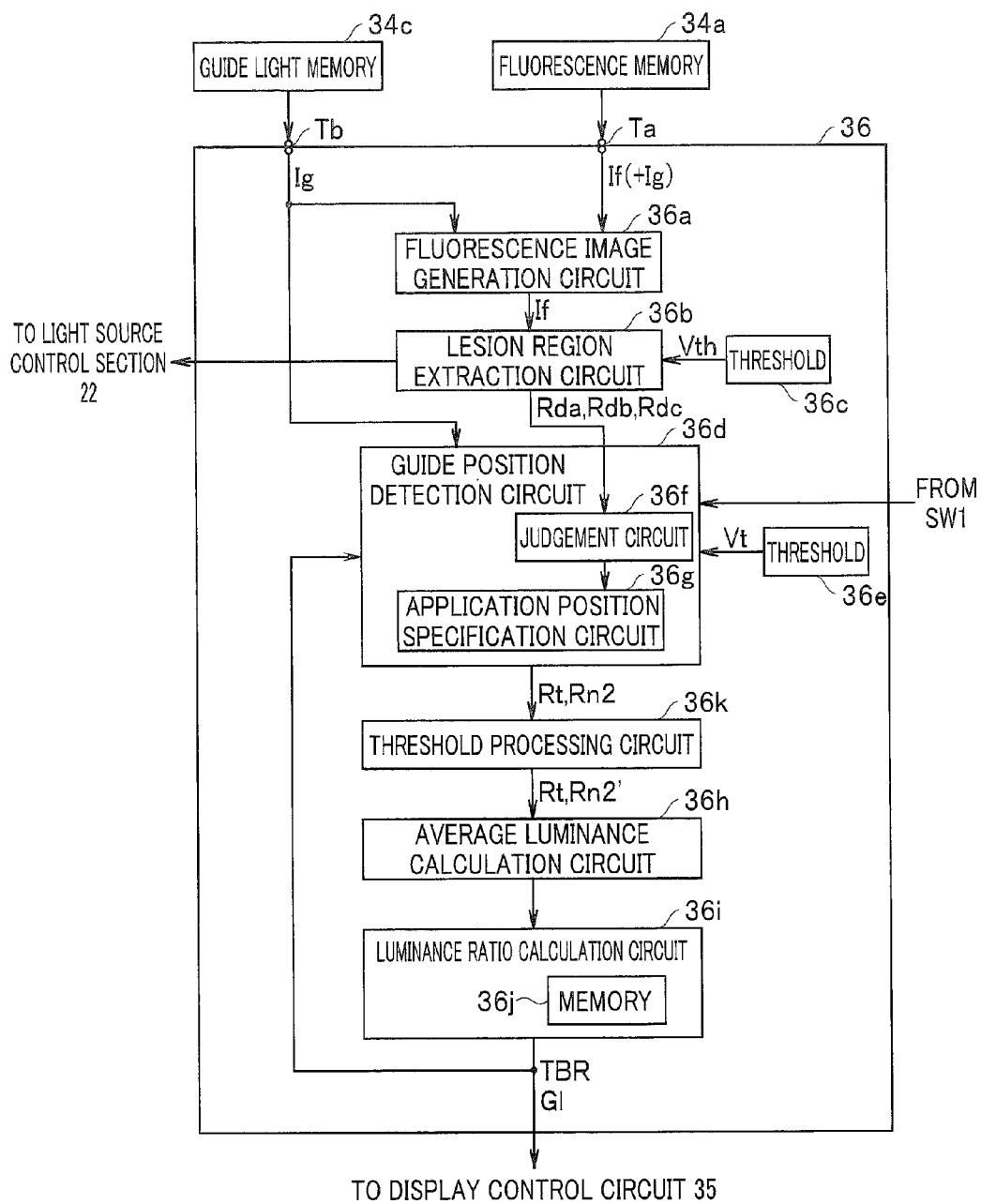
FIG. 10 is a block diagram showing a configuration of a contrast calculation circuit of the modification.

FIG. 10 shows a configuration of the contrast calculation circuit 36 in the present modification. The information of the application region Rt and the non-application region Rn2 specified by the application position specification circuit 36g is inputted to the threshold processing circuit 36k, and the threshold processing circuit 36k executes threshold processing corresponding to the case with a plurality of regions Rd of the lesion part to accurately calculate the luminance ratio.

Hereinafter, operation of the present modification will be described. Only part of the operation of the present modification is different from the operation in the first embodiment, and therefore, only the different part will be described.

Figure 11A:
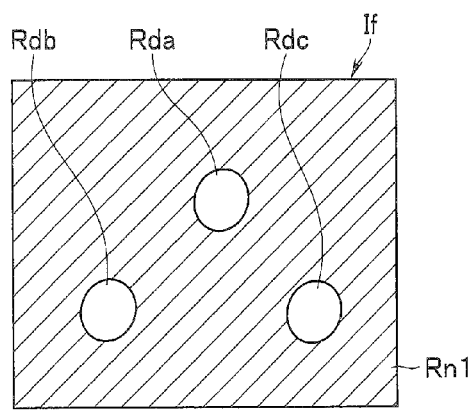
FIG. 11A is a diagram showing a plurality of regions of the lesion part extracted on the fluorescence image.

In the case of the present modification, the lesion region extraction circuit 36b in the contrast calculation circuit 36 extracts a plurality of regions Rda, Rdb, and Rdc of the lesion part as regions of the lesion part with luminance values equal to or greater than the threshold Vth as shown for example in FIG. 11A. A region other than the plurality of regions Rda, Rdb, and Rdc of the lesion part is the region Rn1 of the normal part.

For the plurality of regions Rda, Rdb, and Rdc of the lesion part, the surgeon sets the application region of the applied guide light to one region Rda of the lesion part. Subsequently, the surgeon applies the therapeutic light to the one region Rda of the lesion part as in the case of the first embodiment, and the application position specification circuit 36g specifies the application region Rt and the non-application region Rn2 of the therapeutic light.

Figure 11B:
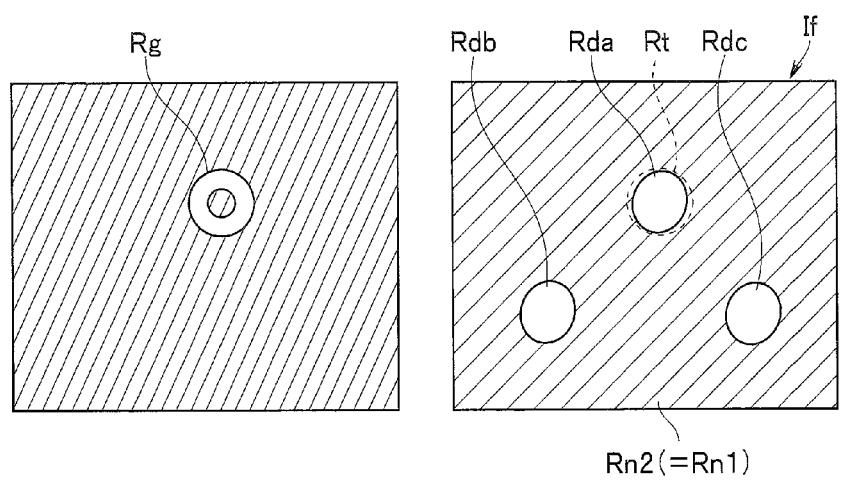
FIG. 11B is an explanatory diagram of a case that the guide light image is used to apply the therapeutic light to one region of the lesion part in FIG. 11A.

FIG. 11B schematically shows the guide light image Ig, the region Rda of the lesion part included in the application region Rt of the therapeutic light (indicated by a dotted line), and the regions Rdb and Rdc of the lesion part not provided with the therapeutic light. A region indicated by oblique lines in the non-application region Rn2 is the region Rn1 of the normal part.

In this case, the non-application region Rn2 includes the regions Rdb and Rdc of the lesion part. Therefore, in the present modification, the threshold processing circuit 36k uses, for example, the threshold Vth, which is used by the lesion region extraction circuit 36b to extract the lesion region, to remove a region with a luminance value equal to or greater than the threshold Vth in the non-application region Rn2 from the non-application region Rn2 and sets the non-application region, from which the region is removed, as Rn2'.

Figure 12:
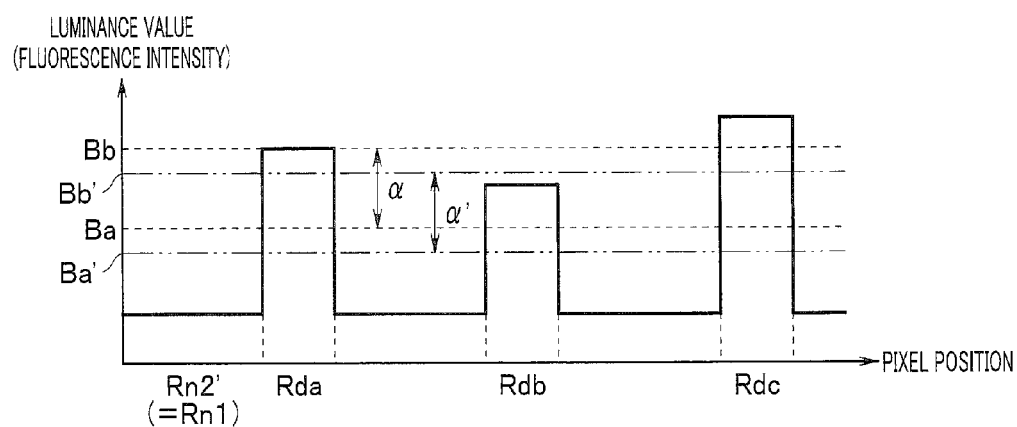
FIG. 12 is a diagram showing a distribution of luminance values at pixel positions of fluorescence pixels forming the fluorescence image.

FIG. 12 schematically shows a distribution of the luminance values (fluorescence intensities or pixel values) in fluorescence pixels forming the fluorescence image If. Here, the luminance value of the threshold Vth is indicated by Ba.

As shown in FIG. 12, each of the regions Rda, Rdb, and Rdc of the lesion part has a luminance value equal to or greater than the threshold Vth (=Ba), and the region Rda of the lesion part provided with the therapeutic light has, for example, a luminance value Bb.

In the present modification, the non-application region Rn2' corrected by removing the regions Rdb and Rdc of the lesion part with the luminance values equal to or greater than the luminance value Ba from the non-application region Rn2 is adopted as described above. The luminance value in the non-application region Rn2' is the luminance value of the region Rn1 of the normal part (indicated by Rn2=Rn1 in FIG. 12).

For the application region Rt of the therapeutic light and the corrected non-application region Rn2', the average luminance calculation circuit 36h calculates the average luminance values Btav and Bnav of the respective regions as in the first embodiment, and subsequently, the luminance ratio calculation circuit 36i also executes the process as in the first embodiment.

However, after the stop of the application of the therapeutic light to the region Rda of the lesion part, the guide position detection circuit 36d applies a process similar to the case of the first region Rda of the lesion part to the next region Rdb of the lesion part in the present modification.

In this case, the luminance value of the region Rda of the lesion part is a value close to the luminance value of the region Rn1 of the normal part, and the region Rda is included in the corrected non-application region Rn2' along with the region Rn1 of the normal part. In other words, the corrected non-application region Rn2' is a region in which the region Rdc of the lesion part is removed from the first non-application region Rn2 in this case. In this way, the contrast calculation circuit 36 applies a process similar to the case of the first region Rda of the lesion part to the region Rdb of the lesion part. When the treatment based on the application of the therapeutic light to the region Rdb of the lesion part is finished, a process for the remaining region Rdc of the lesion part is executed. In this case, the region of the lesion part equal to or greater than the luminance value Ba is only Rdc, and the process is similar to the case of the first embodiment. In this way, the case of a plurality of regions of the lesion part has effects similar to the case of the first embodiment.

Note that when the therapeutic light is applied to perform the treatment for the lesion region as described above, the luminance value (average) in the application region Rt of the therapeutic light drops (gradually decreases) with a lapse of application time period.

Therefore, when the application region Rt and the corrected non-application region Rn2' are set (or updated) along with the lapse of time, a value of Bb−Ba α in FIG. 12 may be lowered to set (update) the non-application region Rn2' corrected by removing the regions Rdb and Rdc of the lesion part with high luminance values included in the non-application region Rn2.

For example, in the state at the start of the application of the therapeutic light in FIG. 12, the average luminance of the region Rda of the lesion part is Bb indicated by a solid line, and after a lapse of a predetermined time period from the start of the application, the average luminance changes to drop to, for example, Bb' indicated by an alternate long and two short dashes line. The luminance value for detecting (discriminating) the regions Rdb and Rdc of the lesion part with high luminance values included in the non-application region Rn2 of FIG. 11B may be lowered from Ba to, for example, Ba' according to the change.

In other words, along with a lapse of time period from the start of the application, the value of Bb-Ba α may be lowered according to the change in the luminance value (average) of the region Rda of the lesion part in the application region Rt as indicated by a value of Bb'-Ba' α' to detect (discriminate) the regions Rdb and Rdc of the lesion part in the non-application region. The following is a supplementary explanation.

For example, when the application region Rt of the therapeutic light is set to cover the first region Rda of the lesion part, and the application of the therapeutic light can be performed from the start of the application of the therapeutic light to the stop of the application of the therapeutic light based on the setting, the treatment for curing can be performed without considering the change in the application region Rt and the change in the non-application region Rn2'.

However, between the start of the application of the therapeutic light and the stop of the application of the therapeutic light, the application region Rt of the therapeutic light may change, or the positions of the regions Rdb and Rdc of the lesion part of the non-application region Rn2 may change due to, for example, a movement of the subject 5.

In such a case, the change in the application region Rt of the therapeutic light can be figured out from the application region Rg of the guide light, and the application region Rg of the guide light can be moved to perform operation according to the change. However, the regions Rdb and Rdc of the lesion part existing in the application region Rt of the therapeutic light and the non-application region Rn2 may be updated according to the lapse of time period of the application of the therapeutic light.

It can be considered that the luminances of the regions Rdb and Rdc of the lesion part existing in the non-application region Rn2 hardly changes in the state that the therapeutic light is applied to the region Rda of the lesion part. Therefore, there is an option of using the luminance value Ba (threshold Vth) of the case of the first extraction of the lesion region.

In another option, the regions Rdb and Rdc of the lesion part existing in the non-application region Rn2 are detected according to the value of the luminance (average) of the region Rda of the lesion part in the application region Rt of the therapeutic light where the therapeutic light is applied. An example of an advantage of the latter option includes that the option allows handling a case in which the region Rdb of the lesion part exists near the region Rda of the lesion part that is a current treatment target, and the luminance of a region of part of the region Rdb of the lesion part changes (drops) after the application of the therapeutic light (temporarily, for example).

In other words, even when the luminances of the regions Rdb and Rdc of the lesion part existing in the non-application region Rn2 other than the region Rda of the lesion part to be treated are slightly reduced due to the application of the therapeutic light, the regions Rdb and Rdc of the lesion part can be detected and removed from the region of the normal part existing in the non-application region Rn2.

Note that although the contrast calculation circuit 36 executes the image processing to calculate the non-application regions Rn2 and Rn2' of the therapeutic light in the fluorescence image If in the case described above, the user, such as a surgeon, may designate the non-application regions Rn2 and Rn2' of the therapeutic light on the fluorescence image If (or the combined image Ic) from the input apparatus 23 or the like.

When more than certain pixels are not extracted as a result of the threshold processing by the threshold processing circuit 36k, a process of updating (decreasing) the value α may be added.

When, for example, a region (area) of a beam spot of the therapeutic light forming the application region of the therapeutic light is much larger than the region Rd of the lesion part to be treated in the first embodiment, a following correction process can be executed.

Figure 13A:
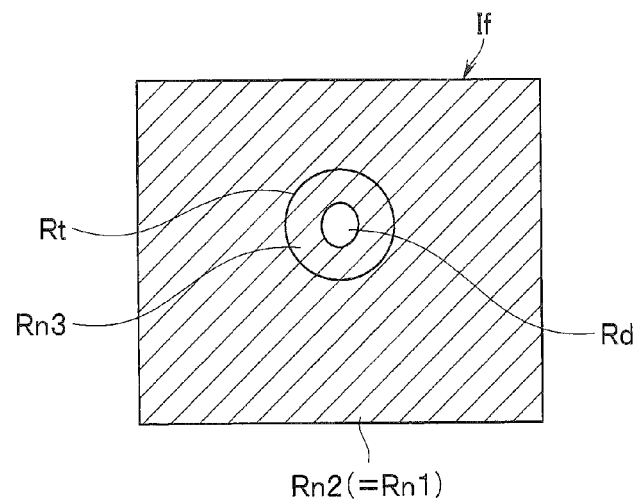
FIG. 13A is a diagram showing a case that an application region of the therapeutic light is much larger than the region of the lesion part.

FIG. 13A shows an explanatory diagram of a case in which the application region Rt of the therapeutic light indicated by a solid line is much larger than the region Rd of the lesion part. In this case, when the average luminance value of the application region Rt of the therapeutic light is calculated in the fluorescence image If, the calculated average luminance value is different from the average luminance value of the region Rd of the lesion part to be treated. Therefore, in the calculation of the average luminance value of the application region Rt of the therapeutic light, the contrast calculation circuit 36 executes threshold processing in a threshold processing circuit 36*l* (not shown) like the threshold processing circuit 36k shown in FIG. 10, for example.

However, although the threshold processing circuit 36k executes the threshold processing for extracting the region of the lesion part with a high luminance value in the non-application region Rn2, the threshold processing circuit 36*l* in this case extracts a region (indicated as Rn3) of the normal part with a low luminance value (lower than in the region Rd of the lesion part to be treated) in the application region Rt and calculates a corrected application region Rt' by removing the region Rn3 of the normal part from the application region Rt.

Figure 13B:
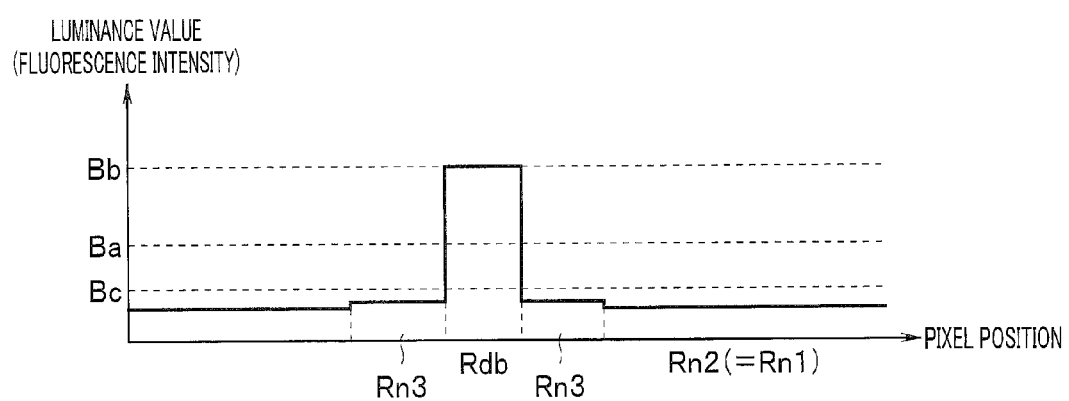
FIG. 13B is an explanatory diagram of operation of removing a region equal to or smaller than a threshold in calculating a luminance of the application region of the therapeutic light.
Figure 13C:
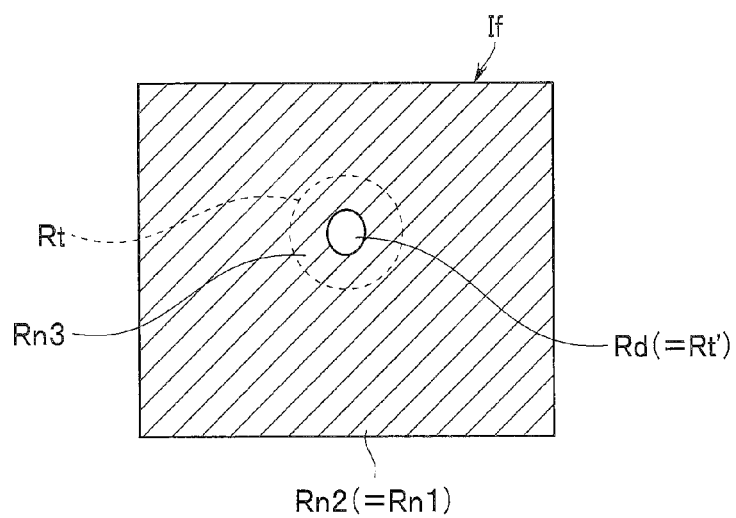
FIG. 13C is a diagram showing, on the fluorescence image, a situation that the region equal to or smaller than the threshold in the application region of the therapeutic light is removed.

FIG. 13B shows an explanatory diagram of the operation by the threshold processing circuit 36*l*. The threshold processing circuit 36*l* uses a threshold with a luminance value Bc that is a little higher than in the region Rn1 of the normal part of the non-application region Rn2 and calculates the application region Rt' by removing the region Rn3 with a luminance value lower than the luminance value Bc in the application region Rt from the application region Rt. That is, the threshold processing circuit 36*l* outputs, to the average luminance calculation circuit 36h, the region Rd of the lesion part with a luminance value higher than a luminance value Bna as the corrected application region Rt' that is a region of the case of calculating the average luminance value in the application region Rt as shown in FIG. 13C.

The average luminance calculation circuit 36h then calculates the average luminance value Btav in the application region Re and the average luminance value Bnav of the non-application region Rn2. The other components are the same as in the first embodiment.

Such a case also has the same effects as in the first embodiment. Note that the value of Bb-Ba may also be changed (gradually reduced) in the case of FIG. 13B according to a lapse of application time period of the therapeutic light.

Figure 13D:
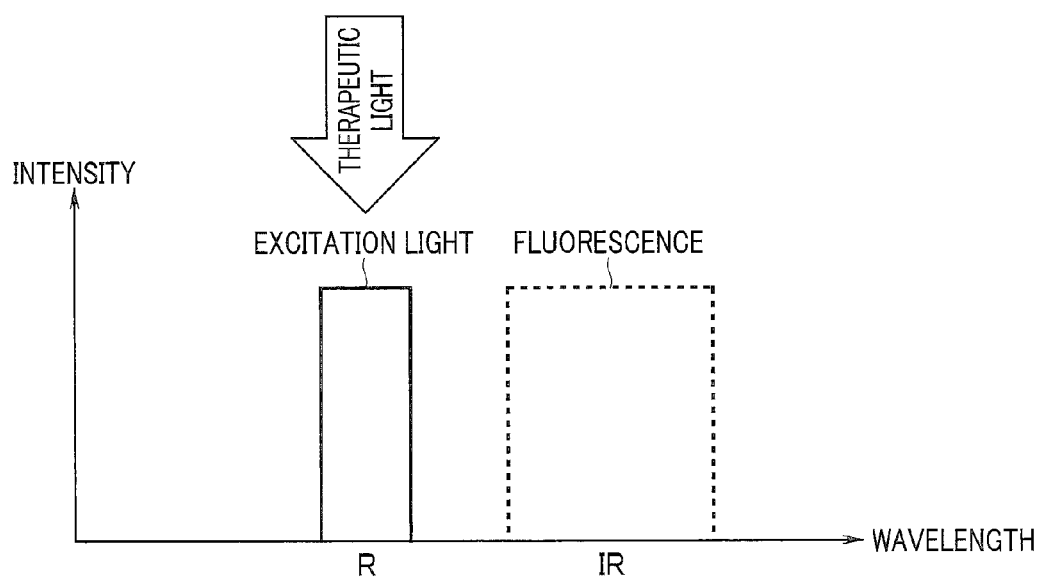
FIG. 13D is a diagram showing an example of setting wavelength bands of the excitation light and the therapeutic light in a case of PIT.

Note that the excitation light and the therapeutic light in the case of performing the treatment based on the PIT in the first embodiment (including the case of the modification) described above were described in the configuration set in a wavelength band as shown in FIG. 13D. In the example shown in FIG. 13D, the therapeutic light and the excitation light are set in a red wavelength band, and the fluorescence in an IR (infrared) band is detected. However, Pan-IR700 may be adopted as an agent for PIT (fluorescent substance) as described below. In this case, the excitation light and the therapeutic light may be set to 790 nm, and the fluorescence with 800 nm may be detected.

A case of performing a treatment based on following PDT will be described as an image processing apparatus of the present invention.

Second Embodiment

Although the case of PIT in which the wavelength band of the excitation light and the wavelength band of the therapeutic light are the same is described in the first embodiment (including the case of the modification) described above, the present invention can also be applied to a case of PDT in which the wavelength band of the excitation light and the wavelength band of the therapeutic light are not the same. Therefore, the case of PDT in which the wavelength band of the excitation light and the wavelength band of the therapeutic light are not the same will be described.

Figure 14:
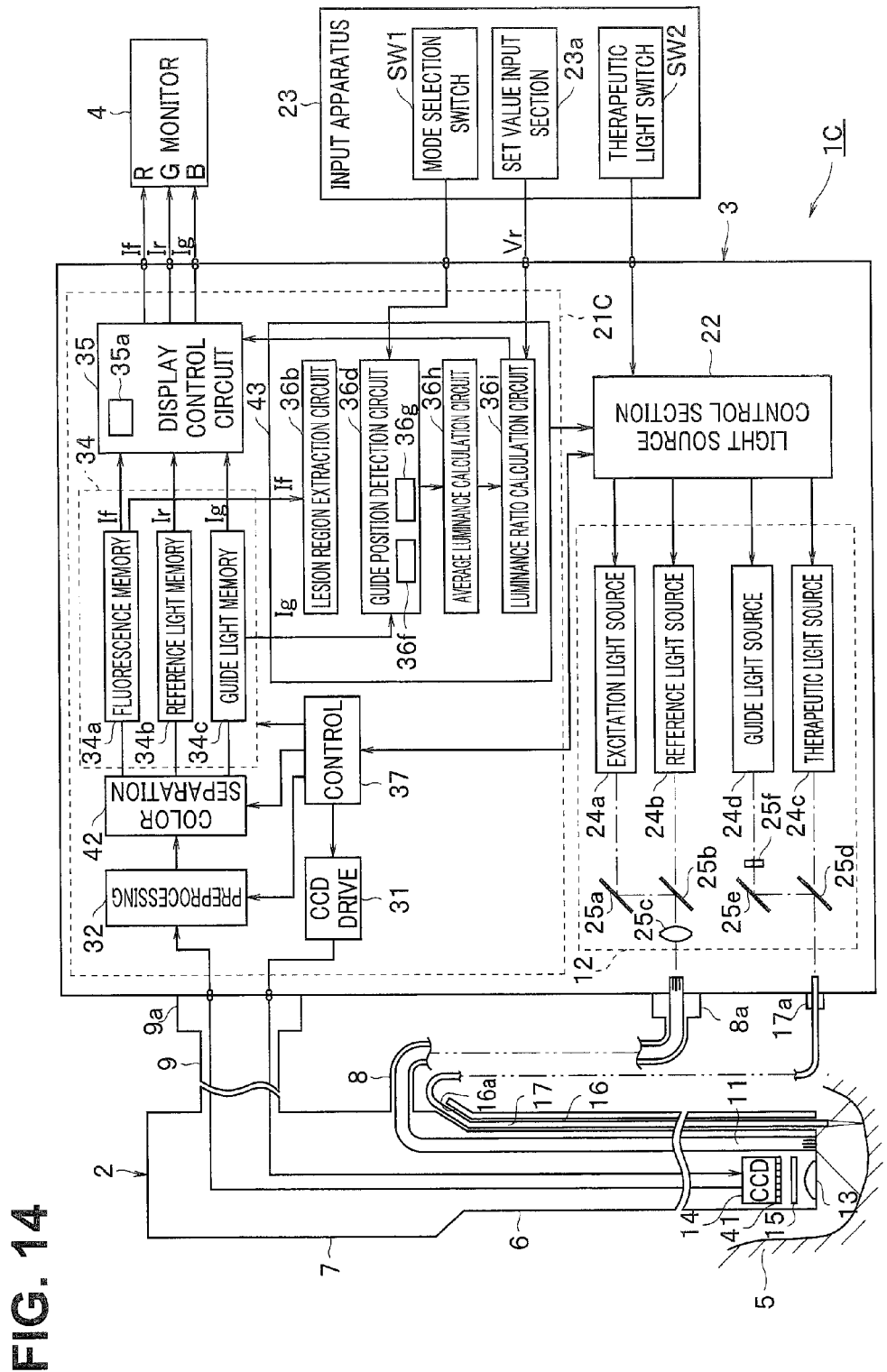
FIG. 14 is a diagram showing an overall configuration of an endoscope apparatus including an image processing apparatus of a second embodiment of the present invention.

FIG. 14 shows a configuration of an endoscope apparatus 1C including the image processing section 21 of a second embodiment of the present invention. The endoscope apparatus 1C includes an endoscope 2C, a control apparatus 3C, the monitor 4, and the input apparatus 23.

The endoscope 2C is provided with color filters 41 configured to optically separate colors on the image pickup surface of the CCD 14 in the endoscope 2 of the first embodiment. The color filters 41 include R, G, and B filters with characteristics for respectively transmitting wavelength bands of R (red), G (green), and B (blue)+IRb (infrared), for example. Therefore, R pixels, G pixels, and B pixels as pixels configured to receive (and photoelectrically convert) the light transmitted through the R, G, and B filters have characteristics as shown in FIG. 15.

The R pixel is sensitive to the fluorescence in the R wavelength band and is not sensitive to the therapeutic light of IRa (infrared) or the guide light of the IRb that are in wavelength bands longer than the wavelength band of the fluorescence. The G pixel is sensitive to the reference light in the G wavelength band.

The B pixel is sensitive to the excitation light in the B wavelength band and the guide light of the IRb and is bimodal.

The excitation light source 24a, the reference light source 24b, the therapeutic light source 24c, and the guide light source 24d of a light source section 12C in the present endoscope apparatus 1C generate the excitation light, the reference light, the therapeutic light, and the guide light with the wavelength bands schematically shown in FIG. 15, respectively.

Figure 16A:
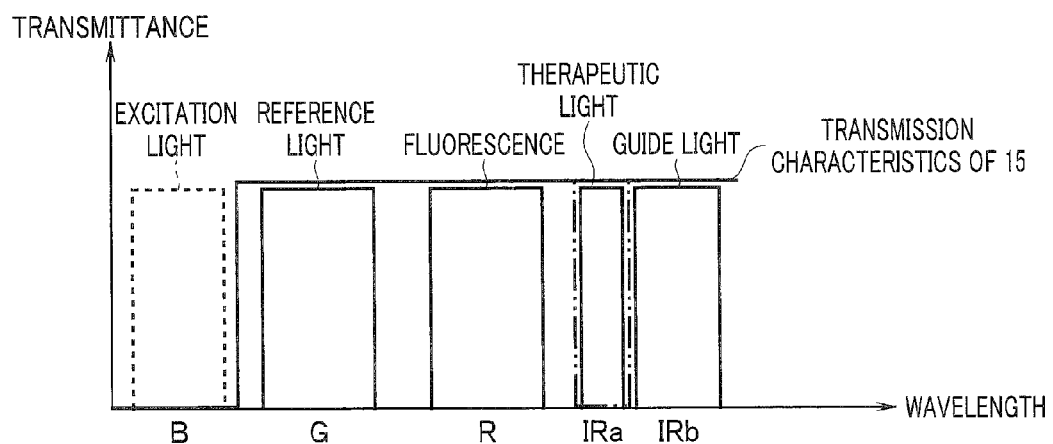
FIG. 16A is a diagram showing characteristics of transmittance of an excitation light cut filter.

The excitation light cut filter 15 in the present endoscope apparatus 1C has characteristics of cutting the excitation light in the B wavelength band and transmitting the light in the other wavelength bands as shown in FIG. 16A. Note that although the excitation light cut filter 15 has characteristics of cutting the excitation light in the B wavelength band, the excitation light cut filter 15 may be set to have transmission characteristics of also cutting the therapeutic light in the infrared wavelength band as indicated by an alternate long and two short dashes line.

That is, the intensity of the fluorescence that the R pixel is sensitive is low. Therefore, the transmission characteristics of the red transmission filter for transmitting the fluorescence and cutting the therapeutic light with a large intensity on the longer wavelength side of the wavelength band of the fluorescence and therapeutic light cut characteristics of the excitation light cut filter 15 may be both used to allow reducing the influence of the therapeutic light in receiving the fluorescence.

In the first embodiment, the monochrome CCD 14 as a monochrome image pickup device is used, and the excitation light and the reference light are frame-sequentially applied. In the present embodiment, the excitation light and the reference light are frame-sequentially applied at the same time. When the guide light is applied, the excitation light, the reference light, and the guide light are applied at the same time, and the therapeutic light is also applied at the same time as the illuminating light.

Figure 16B:
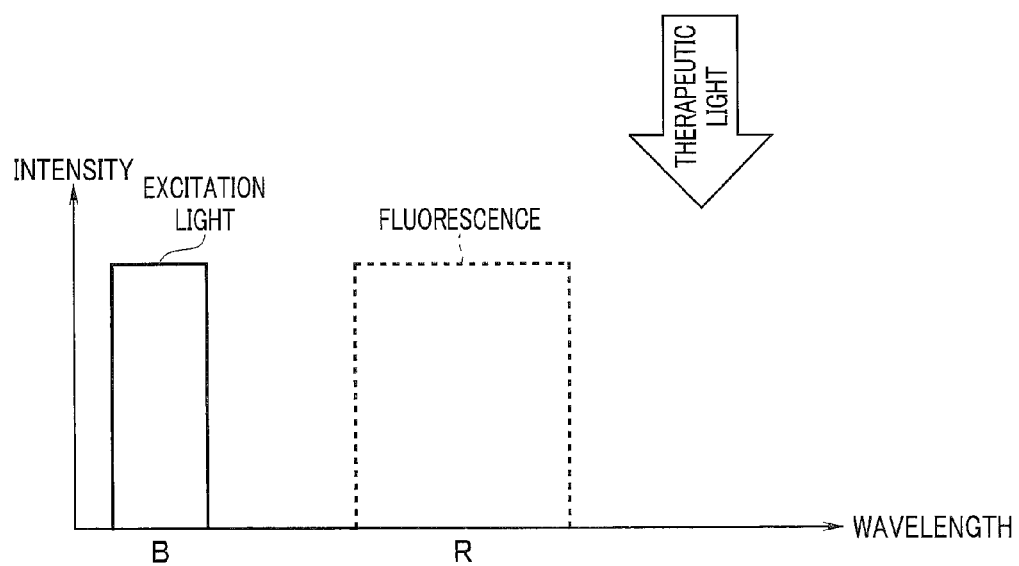
FIG. 16B is a diagram showing an example of setting wavelength bands of the excitation light and the therapeutic light in a case of PDT.

Since the present endoscope apparatus 1C performs the treatment based on PDT as described above, the wavelength band of the excitation light and the wavelength band of the therapeutic light do not coincide, and the wavelength bands are set as in FIG. 16B which illustrates an outline of the wavelength bands. In the example shown in FIG. 16B, the excitation light is set in the B wavelength band, the fluorescence is set in the R wavelength band, and the therapeutic light is set in the infrared wavelength band on the longer wavelength side of the fluorescence. In addition, when a hematoporphyrin derivative is used as the agent for PDT (fluorescent substance), the excitation light (wavelength band of the excitation light) may be set in a wavelength band different from the wavelength band of the therapeutic light in the present endoscope apparatus 1C. The wavelength of the excitation light may be 405 nm, the wavelength band of the therapeutic light may be 630 to 680, and the fluorescence with 635 nm may be detected.

In an image processing section 21C of the present endoscope apparatus 1C, the CDS circuit in the preprocessing circuit 32 extracts signal components, and the A/D conversion circuit in the preprocessing circuit 32 converts the signal components to a digital image signal. The color separation circuit 42 configured to receive the output signal of the preprocessing circuit 32 performs the color separation into the fluorescence image If, the reference light image Ir, and the guide light image Ig (image signals of the images) based on the R pixels, the G pixels, and the B pixels, and the images are respectively stored in the fluorescence memory 34a, the reference light memory 34b, and the guide light memory 34c.

In this way, in the image processing section 21C of the present embodiment, the color separation circuit 42 separates the fluorescence image If, the reference light image Ir, and the guide light image Ig, and the fluorescence memory 34a, the reference light memory 34b, and the guide light memory 34c store the color-separated fluorescence image If, reference light image Ir, and guide light image Ig. That is, the fluorescence memory 34a also outputs the fluorescence image If in the state that the guide light is applied. Furthermore, the display control circuit 35 does not require the subtraction circuit 35a.

Figure 17:
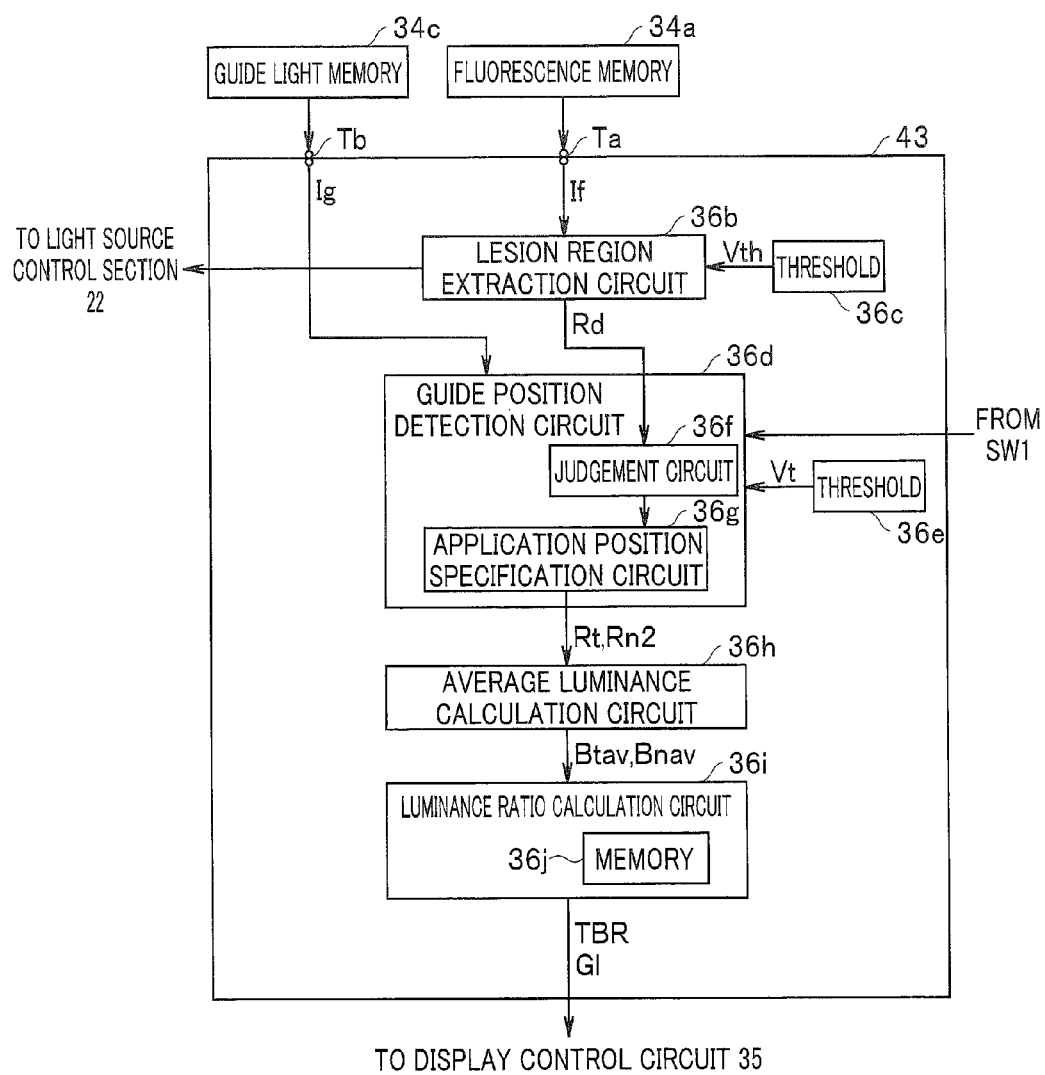
FIG. 17 is a block diagram showing a configuration of a contrast calculation circuit of the second embodiment.

Therefore, in a contrast calculation circuit 43 shown in FIG. 14 or 17 in the present embodiment, the fluorescence image generation circuit 36a in the contrast calculation circuit 36 shown in FIG. 1 or 3 is deleted. The contrast calculation circuit 43 has the same effects as in the first embodiment.

Figure 18:
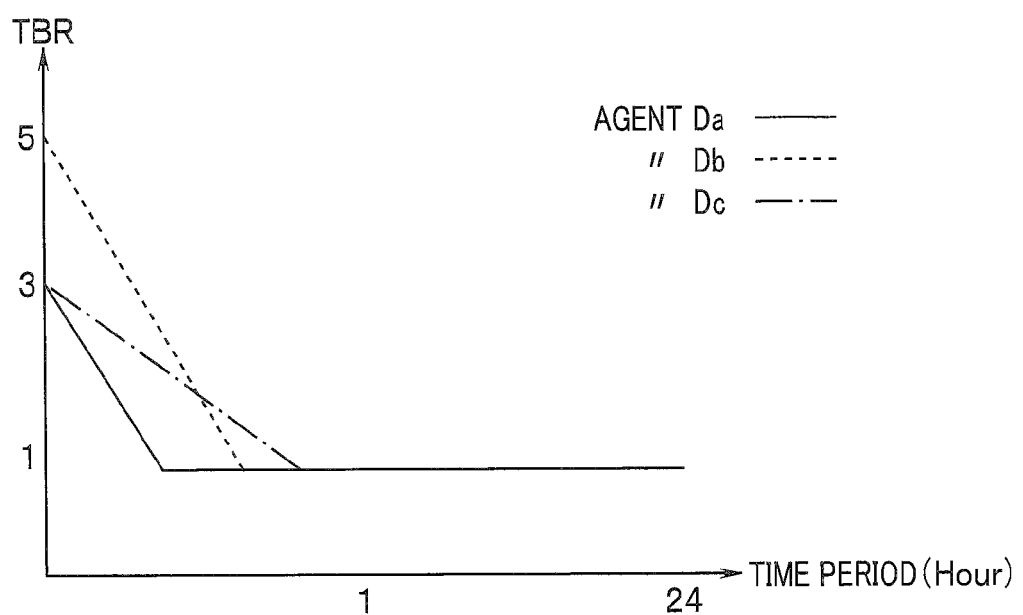
FIG. 18 is a diagram showing a situation that characteristics of a change in the luminance ratio relative to a time period of the application of the therapeutic light vary according to agents in a case of performing a treatment of PDT.

Note that as shown in FIG. 6B, the TBR changes due to the time change from the time of the start of the application of the therapeutic light. In this case, the temporal change of TBR may vary according to PDT agents Da, Db, and Dc as shown for example in FIG. 18.

Therefore, the threshold and the like may be changed according to the agent used for the treatment (administered to the subject 5).

As shown in FIG. 6B, a prediction change of TBR after a latest time may be calculated from a plurality of values of TBR calculated before the latest time (t4 in FIG. 6B), and the prediction change may be displayed as indicated by an alternate long and two short dashes line. A time tpr that the value reaches the set value Vr may be calculated and displayed. For example, the prediction circuit 36m indicated by a dotted line in the luminance ratio calculation circuit 36i in FIG. 3 may perform the calculation.

Note that the above described embodiments and the like may be partially combined to form different embodiments.

What is claimed is:

1. An image processing apparatus comprising:
   an input section configured to receive fluorescence image information obtained by picking up an image of fluorescence based on application of excitation light to a subject provided with a fluorescent substance with a specific effect on a living tissue and therapeutic light position image information including an application position of therapeutic light for causing the fluorescent substance to make an effect on a living body;
   a specification section configured to specify an application region of the therapeutic light in the fluorescence image information based on the therapeutic light position image information inputted to the input section;
   an extraction section configured to extract a luminance value corresponding to the application region of the therapeutic light specified by the specification section in the fluorescence image information inputted to the input section and a luminance value corresponding to a region other than the application region of the therapeutic light in the fluorescence image information; and
   a calculation section configured to calculate and output a ratio of the luminance value corresponding to the application region extracted by the extraction section to the luminance value corresponding to the region other than the application region.

2. The image processing apparatus according to claim 1, further comprising
   a memory configured to output information regarding a progression of the effect on the living body based on the ratio calculated by the calculation section.

3. The image processing apparatus according to claim 2, wherein
   the memory generates change information indicating a temporal change in the ratio after start of the application of the therapeutic light and displays the change information on a display apparatus configured to display the fluorescence image.

4. The image processing apparatus according to claim 2, further comprising:
   a set value input circuit configured to input a set value for stopping the application of the therapeutic light; and a controller configured to perform control for stopping the application of the therapeutic light when the ratio calculated by the calculation section or a value calculated based on the ratio becomes a value corresponding to the set value.

5. The image processing apparatus according to claim 2, wherein
   the memory uses a plurality of times after a time of a start of the application of the therapeutic light and a plurality of values of the ratio respectively calculated by the calculation section in the plurality of times to calculate prediction values of the values of the ratio in time periods after a current time and outputs the prediction values to the display apparatus.

6. The image processing apparatus according to claim 1, wherein
   the extraction section extracts a region with a luminance value lower than the luminance value corresponding to the application region of the therapeutic light by a predetermined value or more, as the region other than the application region of the therapeutic light.

7. The image processing apparatus according to claim 6, wherein
   the extraction section extracts the region other than the application region of the therapeutic light by setting the predetermined value to a value that decreases with an increase in a time period of the application of the therapeutic light.

8. The image processing apparatus according to claim 1, wherein
   the calculation section uses an average luminance value in the application region of the therapeutic light as the luminance value corresponding to the application region of the therapeutic light and uses an average luminance value in the region other than the application region of the therapeutic light as the luminance value of the region other than the application region of the therapeutic light to calculate the ratio.

9. The image processing apparatus according to claim 1, further comprising:
   a controller configured to:
   perform control for generating, as the therapeutic light position image information, guide light image information including an application region of guide light corresponding to the application region of the therapeutic light; and
   perform control for generating the fluorescence image information by picking up an image of the fluorescence,
   wherein the specification section specifies a region with a luminance value exceeding a predetermined threshold in the guide light image information as the application region of the guide light and specifies a region in the fluorescence image information corresponding to the specified application region of the guide light as the application region of the therapeutic light.

10. The image processing apparatus according to claim 1, further comprising
    a lesion region extraction section configured to extract, as a lesion region, a region with a luminance equal to or greater than a predetermined luminance value in the fluorescence image information, wherein
    when the application region of the therapeutic light is set to include at least part of the lesion region extracted by the lesion region extraction section,
    if the specification section judges that a correspondence region corresponding to the region other than the application region of the therapeutic light in the fluorescence image information includes a region with a luminance equal to or greater than the predetermined luminance value, the specification section extracts a luminance value of the correspondence region by excluding the judged region.

11. The image processing apparatus according to claim 1, further comprising
    a lesion region extraction section configured to extract, as a lesion region, a region with a luminance equal to or greater than a predetermined luminance value in the fluorescence image information, wherein when the application region of the therapeutic light is set to include an entirety of the lesion region extracted by the lesion region extraction section, if the application region of the therapeutic light includes a low luminance region equal to or smaller than a threshold set lower than the predetermined luminance value, the specification section extracts a luminance value corresponding to the application region of the therapeutic light by excluding the low luminance region.

12. An image processing apparatus comprising:
a computer processor configured to:
receive fluorescence image information obtained by picking up an image of fluorescence based on application of excitation light to a subject provided with a fluorescent substance with a specific effect on a living tissue and therapeutic light position image information including an application position of therapeutic light for causing the fluorescent substance to make an effect on a living body;
specify an application region of the therapeutic light in the fluorescence image information based on received the therapeutic light position image information;
extract a first luminance value corresponding to the specified application region of the therapeutic light and a second luminance value corresponding to a region other than the application region of the therapeutic light; and
calculate and output a ratio of the first luminance value to the second luminance value.

13. The image processing apparatus according to claim 12, wherein the computer processor is further configured to:
output information regarding a progression of the effect on the living body based on the ratio of the first luminance value to the second luminance value.

14. The image processing apparatus according to claim 13, wherein the computer processor is further configured to generate change information indicating a temporal change in the ratio after start of the application of the therapeutic light and display the change information on a display apparatus configured to display the fluorescence image.

15. The image processing apparatus according to claim 13, wherein the computer processor is further configured to use a plurality of times after a time of a start of the application of the therapeutic light and a plurality of values of the ratio respectively calculated in the plurality of times to calculate prediction values of the values of the ratio in time periods after a current time and outputs the prediction values to the display apparatus.

16. The image processing apparatus according to claim 12, wherein the computer processor is further configured to extract a region with a luminance value lower than the first luminance value by a predetermined value or more, as the region other than the application region of the therapeutic light.

17. The image processing apparatus according to claim 16, wherein the computer processor is further configured to extract the region other than the application region of the therapeutic light by setting the predetermined value to a value that decreases with an increase in a time period of the application of the therapeutic light.

18. The image processing apparatus according to claim 12, wherein the computer processor is further configured to use an average luminance value in the application region of the therapeutic light as the first luminance value and use an average luminance value in the region other than the application region of the therapeutic light as the second luminance value to calculate the ratio.

19. The image processing apparatus according to claim 12, wherein the computer processor is further configured to extract, as a lesion region, a region with a luminance equal to or greater than a predetermined luminance value in the fluorescence image information, wherein
when the application region of the therapeutic light is set to include at least part of the extracted lesion region,
responsive to judging that a correspondence region corresponding to the region other than the application region of the therapeutic light in the fluorescence image information includes a region with a luminance equal to or greater than the predetermined luminance value, the computer processor extracts a luminance value of the correspondence region by excluding the judged region.

20. The image processing apparatus according to claim 12, wherein the computer processor is further configured to extract, as a lesion region, a region with a luminance equal to or greater than a predetermined luminance value in the fluorescence image information, wherein
when the application region of the therapeutic light is set to include an entirety of the extracted lesion region,
responsive to judging that the application region of the therapeutic light includes a low luminance region equal to or smaller than a threshold set lower than the predetermined luminance value, the computer processor extracts a luminance value corresponding to the application region of the therapeutic light by excluding the low luminance region.

* * * * *